(12) United States Patent
Grossmann et al.

(10) Patent No.: US 11,788,081 B2
(45) Date of Patent: Oct. 17, 2023

(54) PROTEIN MACROCYCLIZATION

(71) Applicant: Stichting VU, Amsterdam (NL)

(72) Inventors: Tom Norbert Grossmann, Amstelveen (NL); Marta Pelay Gimeno, Leiden (NL); Sven Hennig, Amsterdam (NL); Saskia Antonie Neubacher, Amstelveen (NL)

(73) Assignee: Stichting VU, Amsterdam (NL)

( * ) Notice: Subject to any disclaimer, the term of this patent is extended or adjusted under 35 U.S.C. 154(b) by 0 days.

(21) Appl. No.: 17/048,284

(22) PCT Filed: Apr. 18, 2019

(86) PCT No.: PCT/NL2019/050229
§ 371 (c)(1),
(2) Date: Oct. 16, 2020

(87) PCT Pub. No.: WO2019/203645
PCT Pub. Date: Oct. 24, 2019

(65) Prior Publication Data
US 2021/0102185 A1  Apr. 8, 2021

(30) Foreign Application Priority Data
Apr. 19, 2018 (EP) .................................... 18168298

(51) Int. Cl.
*C12N 9/96* (2006.01)
*C12N 9/52* (2006.01)
*C12N 15/113* (2010.01)

(52) U.S. Cl.
CPC .............. *C12N 9/52* (2013.01); *C12N 15/113* (2013.01); *C12Y 304/2207* (2013.01)

(58) Field of Classification Search
None
See application file for complete search history.

(56) References Cited

U.S. PATENT DOCUMENTS 7,928,199 B2 * 4/2011 Griffin ................. C07K 1/1075
530/383
2018/0311300 A1  11/2018  Beswick et al.

FOREIGN PATENT DOCUMENTS

| EP | 3929587 A1 | 12/2021 |
|---|---|---|
| JP | 2005-500831 A | 1/2005 |
| WO | 2014078623 A2 | 5/2014 |
| WO | 2018197893 A1 | 11/2018 |
| WO | 2019034866 A1 | 2/2019 |
| WO | 2019203645 A1 | 10/2019 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*

Moore et al. "Enzyme stabilization via computationally guided protein stapling" 12472-12477, PNAS, Nov. 21, 2017, vol. 114, No. 47.

Dang et al. "De novo design of covalently constrained mesosize protein scaffolds with unique tertiary structures". 10852-10857, PNAS, Oct. 10, 2017, vol. 114, No. 41.

Chen et al. "Structurally Diverse Cyclisation Linkers Impose Different Backbone Conformations in Bicyclic Peptides", CHEMBIOCHEM, (May 7, 2012), vol. 13, No. 7, doi:10.1002/cbic.201200049, ISSN 1439-4227, pp. 1032-1038.

Angelini et al. "Chemical Macrocyclization of Peptides Fused to Antibody Fc Fragments", Bioconjugate Chemistry, US, (Sep. 19, 2012), vol. 23, No. 9, doi:10.1021/bc300184m, ISSN 1043-1802, pp. 1856-1863.

Diderich et al. "Directed Evolution of Bicyclic Peptides for Therapeutic Application", Chimia International Journal for Chemistry, (Dec. 18, 2013), vol. 67, No. 12, doi:10.2533/chimia.2013.910, ISSN 0009-4293, pp. 910-915.

Bashiruddin et al. "Synthesis of fused tricyclic peptides using a reprogrammed translation system and chemical modification", Bioorganic Chemistry., US, (Aug. 1, 2015), vol. 61, doi:10.1016/j.bioorg.2015.06.002, ISSN 0045-2068, pp. 45-50.

Lau et al. Peptide Stapling Techniques Based on Different Macrocyclisation Chemistries. Chem. Soc. Rev. 2015, 44 (1), 91-102. https://doi.org/10.1039/C4CS00246F.

Yuan et al. Prediction of Protein Accessible Surface Areas by Support Vector Regression. Proteins: Structure, Function, and Bioinformatics 2004, 57 (3), 558-564. https://doi.org/10.1002/prot.20234.

Faraggi et al. Accurate Single-Sequence Prediction of Solvent Accessible Surface Area Using Local and Global Features. Proteins: Structure, Function, and Bioinformatics 2014, 82 (11), 3170-3176. https://doi.org/10.1002/prot.24682.

Mattson et al. A Practical Approach to Crosslinking. Mol Biol Rep 1993, 17 (3), 167-183. https://doi.org/10.1007/BF00986726.

Paramelle et al. Chemical Cross-Linkers for Protein Structure Studies by Mass Spectrometry. Proteomics 2013, 13 (3-4), 438-456. https://doi.org/10.1002/pmic.201200305.

Liu et al. Enhancing protein stability with extended disulfide bonds. Proc. Natl. Acad. Sci. USA 2016, 113, 5910-5915.

Chen et al. Genetically Encoding an Electrophilic Amino Acid for Protein Stapling and Covalent Binding to Native Receptors. ACS Chem. Biol. 2014, 9, 1956-1961.

Li et al. Enhancing Protein Stability with Genetically Encoded Noncanonical Amino Acids. J. Am. Chem. Soc. 2018, 140, 15997-16000.

Lin et al. Influence of an Extrinsic Cross-Link on the folding Pathway of Ribonuclease A. Conformational and Thermodynamic Analysis of Cross-Linked (Lysine7-Lysine41)-Ribonuclease A., Biochemistry 1984, 23, 5504-5512.

Weber et al. The 2-A resolution structure of a thermostable ribonuclease A chemically cross-linked between lysine residues 7 and 41. Proc. Natl. Acad. Sci. USA 1985, 82, 8473-8477.

(Continued)

*Primary Examiner* — Richard G Hutson

(74) *Attorney, Agent, or Firm* — Banner & Witcoff, Ltd.

(57) ABSTRACT

The present invention relates to methods and cross-linkers for the macrocyclization of proteins. The invention is useful for increasing the stability of a protein.

5 Claims, 26 Drawing Sheets

Specification includes a Sequence Listing.

(56) References Cited

OTHER PUBLICATIONS

Bornscheuer et al. Engineering the third wave of biocatalysis. Nature 2012, 485, 185-194.
Hackenberger et al. Chemoselective Ligation and Modification Strategies for Peptides and Proteins. Angew. Chem. Int. Ed. 2008, 47, 10030-10074.
Keefe et al. Poly(zwitterionic)protein conjugates offer increased stability without sacrificing binding affinity or bioactivity. Nat. Chem. 2012, 4, 59-63.
Harris et al. Effect of Pegylation on Pharmaceuticals. Nat. Rev. Drug Discov. 2003, 2, 214-221.
Reetz. The Importance of Additive and Non-Additive Mutational Effects in Protein Engineering. Angew. Chem. Int. Ed. 2013, 52, 2658-2666.
Jost et al. Engineered proteins with desired specificity: DARPins, other alternative scaffolds and bispecific IgGs. Curr. Opin. Struct. Biol. 2014, 27, 102-112.
Magliery. Protein stability: computation, sequence statistics, and new experimental methods. Curr. Opin. Struct. Biol. 2015, 33, 161-168.
Chapman et al. Scratching the Surface: Resurfacing Proteins to Endow New Properties and Function. Cell Chem. Biol. 2016, 23, 543-553.
Agostini et al. Biocatalysis with Unnatural Amino Acids: Enzymology Meets Xenobiology. Angew. Chem. Int. Ed. 2017, 56, 9680-9703.
Martínez-Sáez et al. Oxetane Grafts Installed Site-Selectively on Native Disulfides to Enhance Protein Stability and Activity In Vivo. Angew. Chem. Int. Ed. 2017, 56, 14963 14967.
Camarero et al. Biosynthesis of a Head-to-Tail Cyclized Protein with Improved Biological Activity. J. Am. Chem. Soc. 1999, 121, 5597-5598.
Iwai et al. Circular L-lactamase: stability enhancement by cyclizing the backbone. FEBS Lett. 1999, 459, 166-172.
Schoene et al. SpyTag/SpyCatcher Cyclization Confers Resilience to Boiling on a Mesophilic Enzyme. Angew. Chem. Int. Ed. 2014, 53, 6101-6104.
Chin. Reprogramming the genetic code. EMBO J. 2011, 30, 2312-2324.
Guimaraes et al. Site-specific C-terminal and internal loop labeling of proteins using sortase-mediated reactions.Nat. Protoc. 2013, 8, 1787-1799.
Bellucci et al. A Noncanonical Function of Sortase Enables Site-Specific Conjugation of Small Molecules to Lysine Residues in Proteins.Angew. Chem. Int. Ed. 2015, 54, 441-445.
Schmohl et al. Sortase-mediated ligations for the site-specific modification of proteins. Curr. Opin. Chem. Biol. 2014, 22, 122-128.
Jo et al. Development of α-Helical Calpain Probes by Mimicking a Natural Protein-Protein Interaction. J. Am. Chem. Soc. 2012, 134, 17704-17713.
Muppidi et al. Rational Design of Proteolytically Stable, Cell-Permeable Peptide Based Selective Mcl-1 Inhibitors. J. Am. Chem. Soc. 2012, 134, 14734-14737.
Diderich et al. Phage Selection of Chemically Stabilized α-Helical Peptide Ligands. ACS Chem. Biol. 2016, 11, 1422-1427.
Spokoyny et al. A Perfluoroaryl-Cysteine SNAr Chemistry Approach to Unprotected Peptide Stapling. J. Am. Chem. Soc. 2013, 135, 5946-5949.
Jafari et al. Discovery of Light-Responsive Ligands through Screening of a Light-Responsive Genetically Encoded Library. ACS Chem. Biol. 2014, 9, 443-450.
Chenna et al. Synthesis and structure activity relationship studies of novel *Staphylococcus aureus* Sortase A inhibitors. Eur. J. Med. Chem. 2010, 45, 3752-3761.
Oh et al. Discovery of Diarylacrylonitriles as a Novel Series of Small Molecule Sortase A Inhibitors. J. Med. Chem. 2004, 47, 2418-2421.
Timmerman et al. Rapid and Quantitative Cyclization of Multiple Peptide Loops onto Synthetic Scaffolds for Structural Mimicry of Protein Surfaces. ChemBioChem 2005, 6, 821-824.
Heinis et al. Phage-encoded combinatorial chemical libraries based on bicyclic peptides. Nat. Chem. Biol. 2009, 5, 502-507.
Chen et al. Peptide Ligands Stabilized by Small Molecules. Angew. Chem. Int. Ed. 2014, 53, 1602-1606.
Cookson. alpha-Synuclein and neuronal cell death. Mol. Neurodegener. 2009, 4, 9.
Porcari, et al. The H50Q Mutation Induces a 10-fold Decrease in the Solubility of Synuclein. J. Biol. Chem. 2015, 290, 2395-2404.
Rosen et al. Capture and Recycling of Sortase A through Site-Specific Labeling with Lithocholic Acid. Angew. Chem. Int. Ed. 2016, 55, 8585-8589.
Wang et al. Proximity-Based Sortase-Mediated Ligation. Angew. Chem. Int. Ed. 2017, 56, 5349-5352.
De Guzman et al. Structural Basis for Cooperative Transcription Factor Binding to the CBP Coactivator. J. Mol. Biol. 2006, 355, 1005-1013.
May 2, 2023 (JP) Office Action Application No. 2020-557254.
Aug. 8, 2023 (EP) Examination Report Application No. 19742978.0.
Jul. 2, 20234 (EP) Search Report Application No. 23157877.4.
Fauser et al. "Current Advances in Covalent Stabilization of Macromolecular Complexes for Structural Biology", Bioconjugate Chemistry, vol. 32, No. 5, Apr. 16, 2021 (Apr. 16, 2021), pp. 879-890, XP093062242, US ISSN: 1043-1802, DOI: 10.1021/acs.bioconjchem.Ic00118.
Piersimoni et al. "Cross-Linking Mass Spectrometry for Investigating Protein Conformations and Protein-Protein Interactions-A Method for All Seasons", Chemical Reviews, vol. 122, No. 8, Nov. 19, 2021 (Nov. 19, 2021), 7500-7531, XP055954246, US ISSN: 0009-2665, DOI: 10.1021/acs.chemrev.Ic00786.
Neubacher et al. "In Situ Cyclization of Proteins (INCYPRO): Cross-Link Derivatization Modulates Protein Stability", The Journal of Organic Chemistry, vol. 85, No. 3, Dec. 2, 2019 (Dec. 2, 2019), pp. 1476-1483, XP093061523, ISSN: 0022-3263, DOI: 10.1021/acs.joc.9b02490 Retrieved from the Internet: URL:http://pubs.acs.org/doi/pdf/10.1021/ac s.joc.9b02490>.
Stadlmeier et al. "A Click-Chemistry-Based Enrichable Crosslinker for Structural and Protein Interaction Analysis by Mass Spectrometry", Chembiochem, John Wiley & Sons, Inc, Hoboken, USA, vol. 21, Nov. 28, 2019 (Nov. 28, 2019), pp. 103-107, XP072203526, ISSN: 1439-4227, DOI: 10.1002/CBIC.201900611.

* cited by examiner

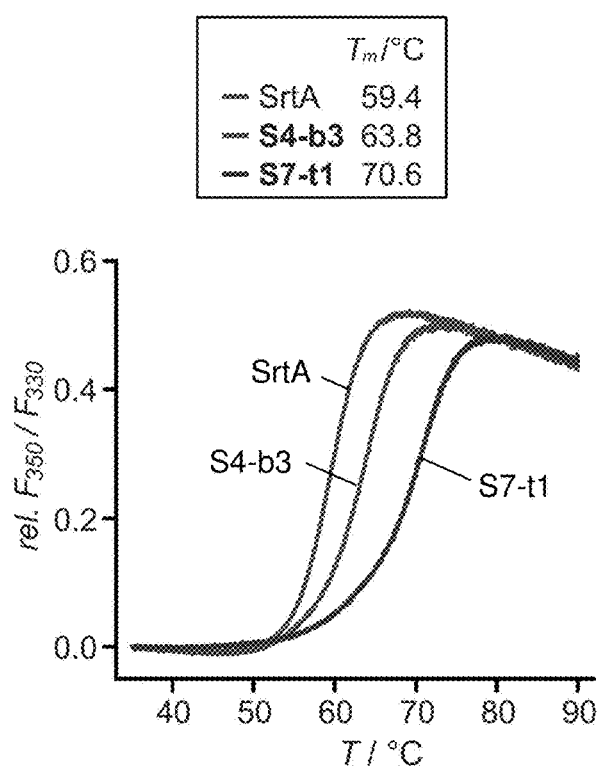
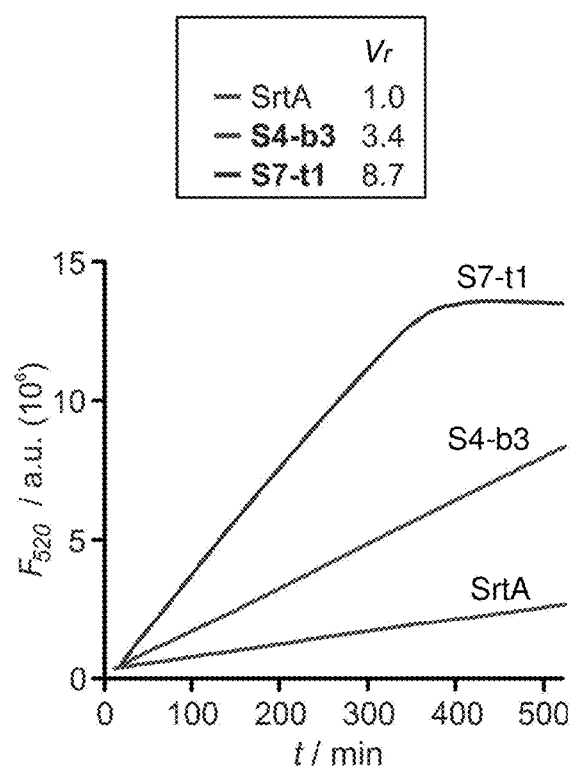
Fig. 3c
Fig. 3d

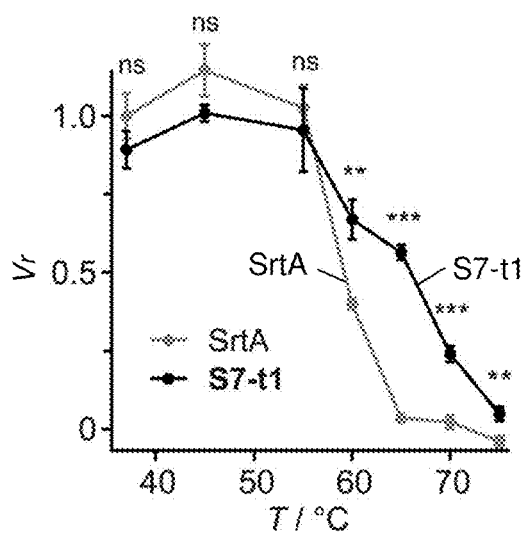
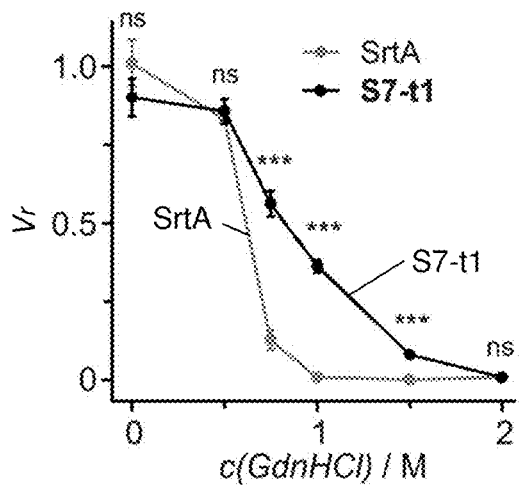
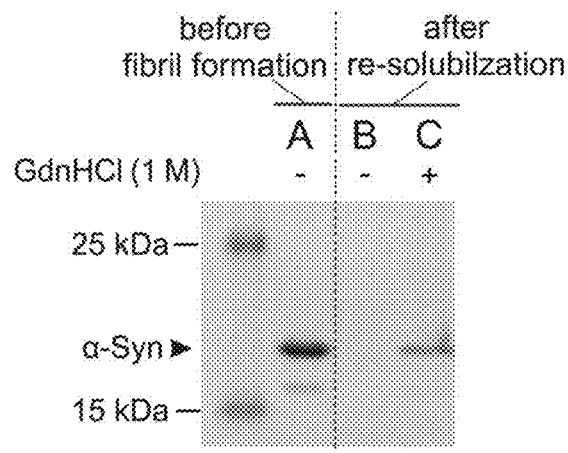
Fig. 4a  Fig. 4b
Fig. 4c  Fig. 4d
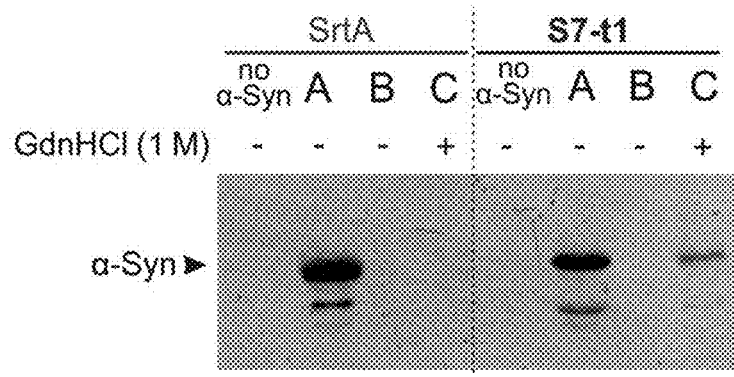
Fig. 4e

```
        60          70          80          90         100
GSHMQ AKPQIPKDKS KVAGYIEIPD ADIKEPVYPG PATPEQLNRG 110         120         130         140         150
VSFAEENESL DDQNISIAGH TEIDRPNYQF TNLKAAKKGS MVYFKVGNET 160         170         180         190         200
RKYKMTSIRD VKPTDVGVLD EQKGKDKQLT LITCDDYNEK TGVWEKRKIF

VATEVK       (SEQ ID NO: 12)
```

Fig. 6a

| Variant | Mutation | Distance ($C_\alpha - C_\alpha$) |
|---|---|---|
| S1 | K134C-D160C | 9.0 Å |
| S2 | K162C-K198C | 8.4 Å |
| S3 | N98C-F122C | 11.2 Å |
| S4 | D111C-E149C | 12.2 Å |
| S5 | E149C-K177C | 16.5 Å |
| S6 | E171C-T203C | 11.8 Å |

Fig. 6b

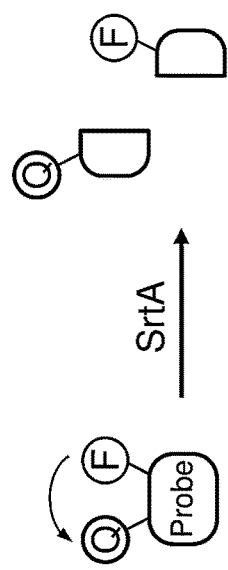
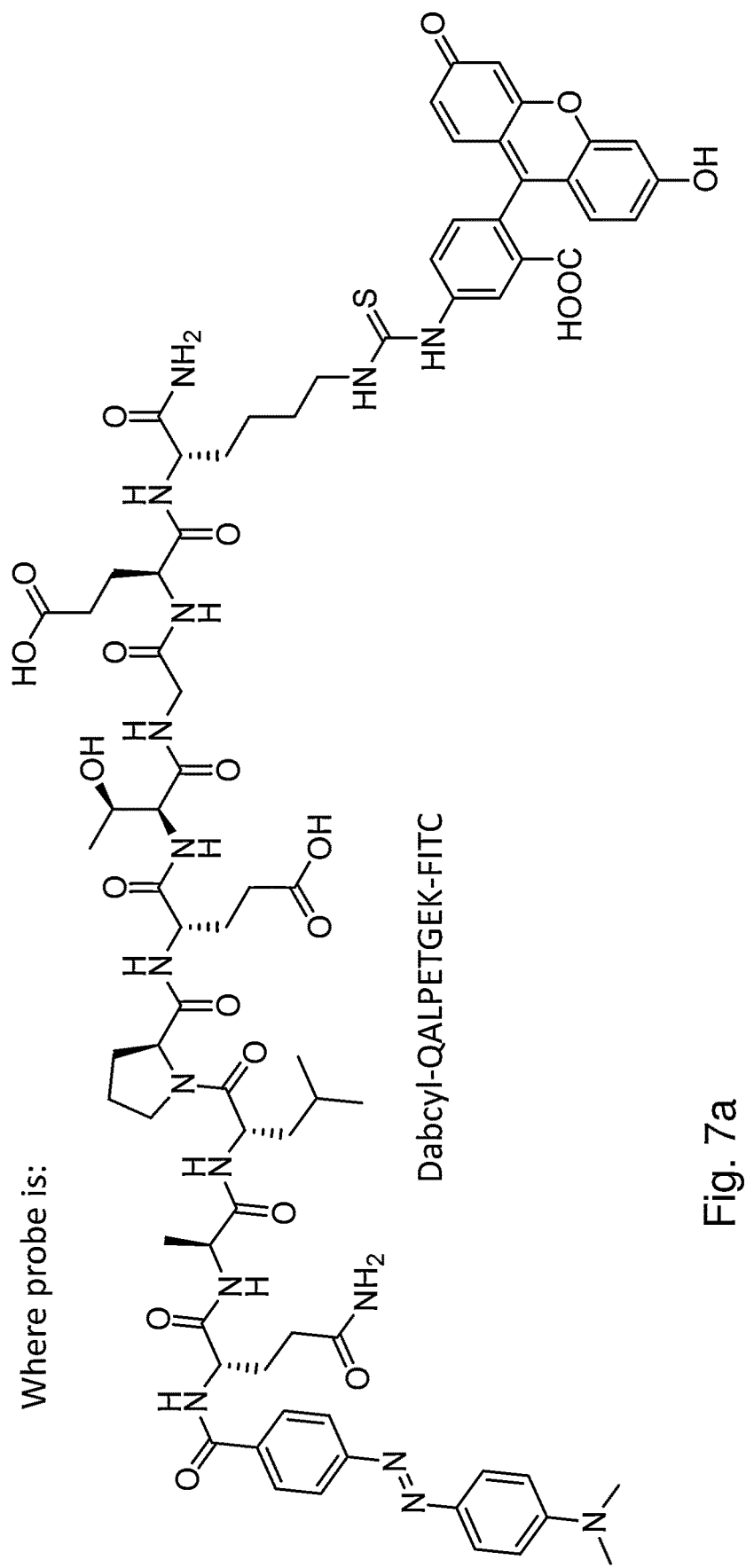
Fig. 7a

GVSFAEENESLCDQNISIAGHTFIDRPNYQFTNLK
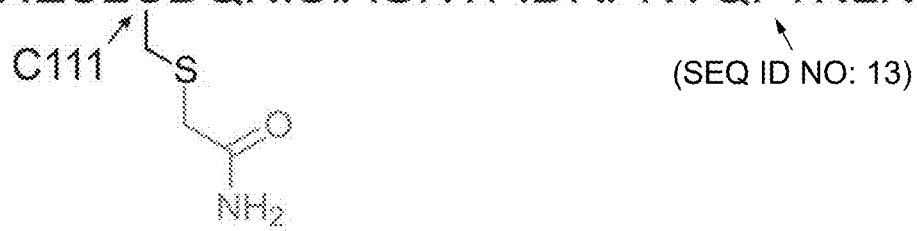
(SEQ ID NO: 13)
molecular formula (monoisotopic m):
$C_{173} H_{261} N_{47} O_{58} S$ (4013.89 g/mol)
calc. monoisotopic peak for $MH^{3+}$:
m/z = 1338.97 th
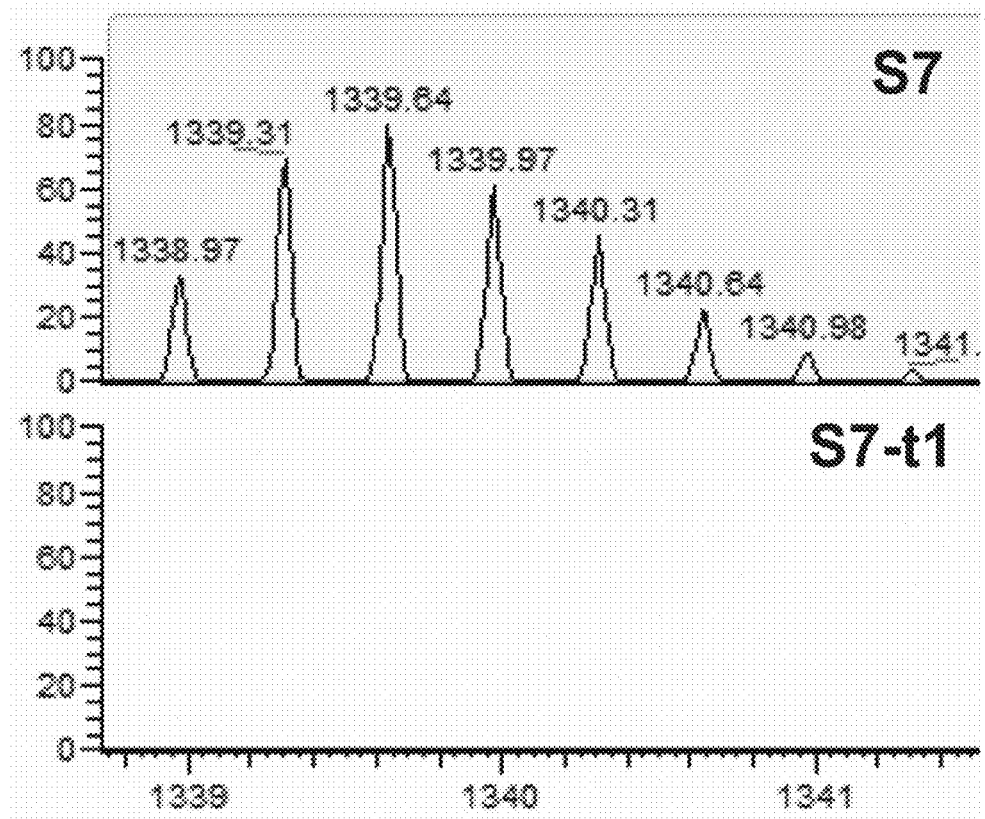
Fig. 8a

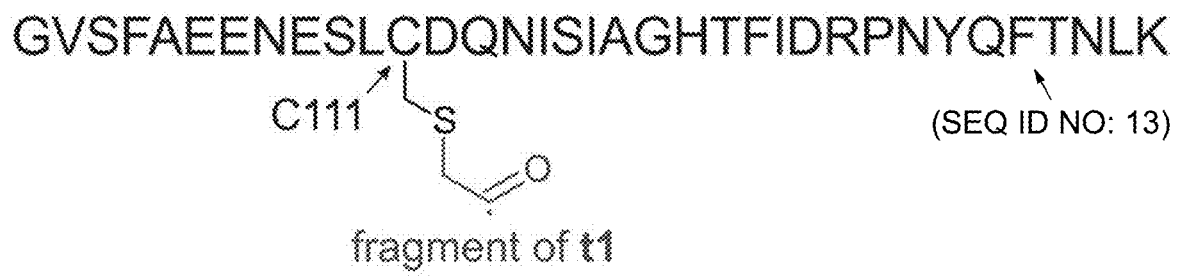
(SEQ ID NO: 13)
fragment of t1
molecular formula (monoisotopic m):
$C_{175} H_{262} N_{47} O_{59} S$ (3997.87 g/mol)
calc. monoisotopic peak for $MH^{3+}$:
m/z = 1333.63 th
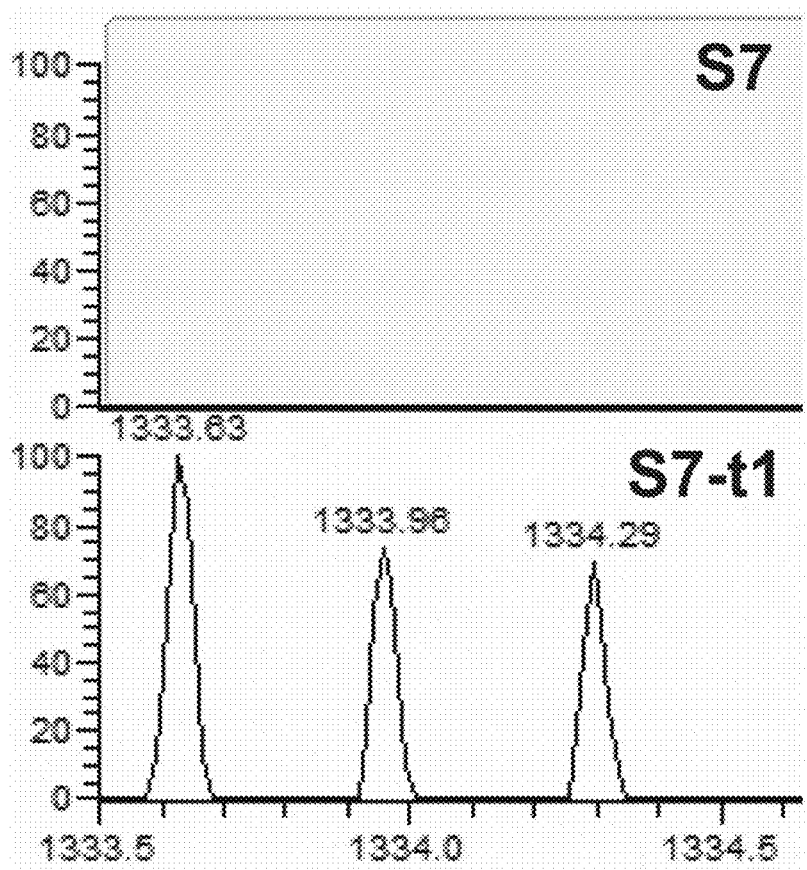
Fig. 8a, Cont'd

KGSMVYFKVGNCTR    (SEQ ID NO: 14)
            C149 molecular formula (monoisotopic m):
$C_{69} H_{112} N_{20} O_{19} S_2$ (1588.79 g/mol)

calc. monoisotopic peak for $MH^{3+}$:
m/z = 530.60 th

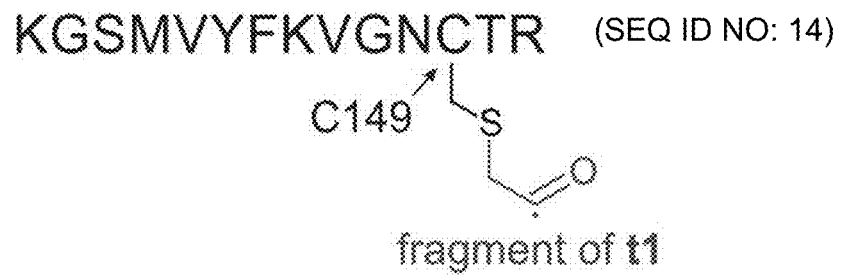
KGSMVYFKVGNCTR (SEQ ID NO: 14)
fragment of t1
molecular formula (monoisotopic m):
$C_{71} H_{113} N_{20} O_{20} S_2$ (1629.79 g/mol)
calc. monoisotopic peak for $MH^{2+}$:
m/z = 815.90 th
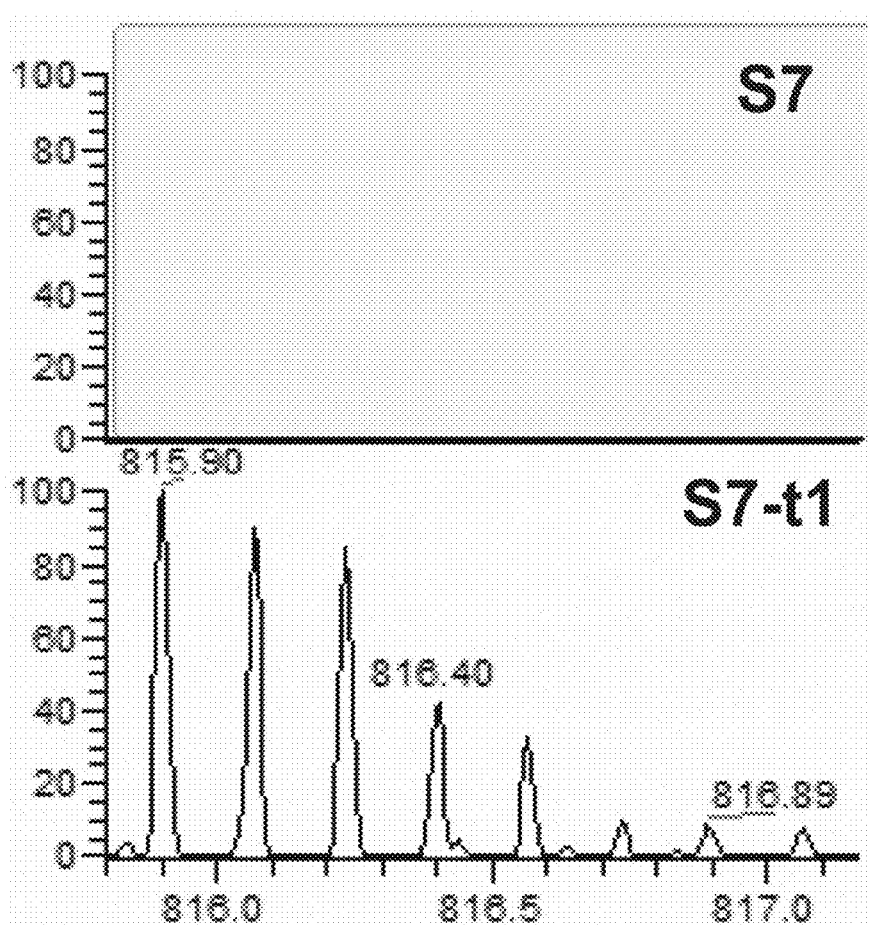
Fig. 8b, Cont'd

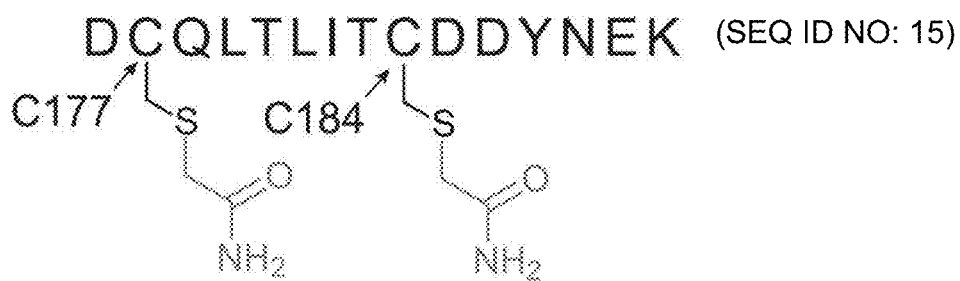
DCQLTLITCDDYNEK (SEQ ID NO: 15)
molecular formula (monoisotopic m):
$C_{77} H_{122} N_{20} O_{31} S_2$ (1886.80 g/mol)
calc. monoisotopic peak for $MH^{3+}$:
m/z = 629.94 th
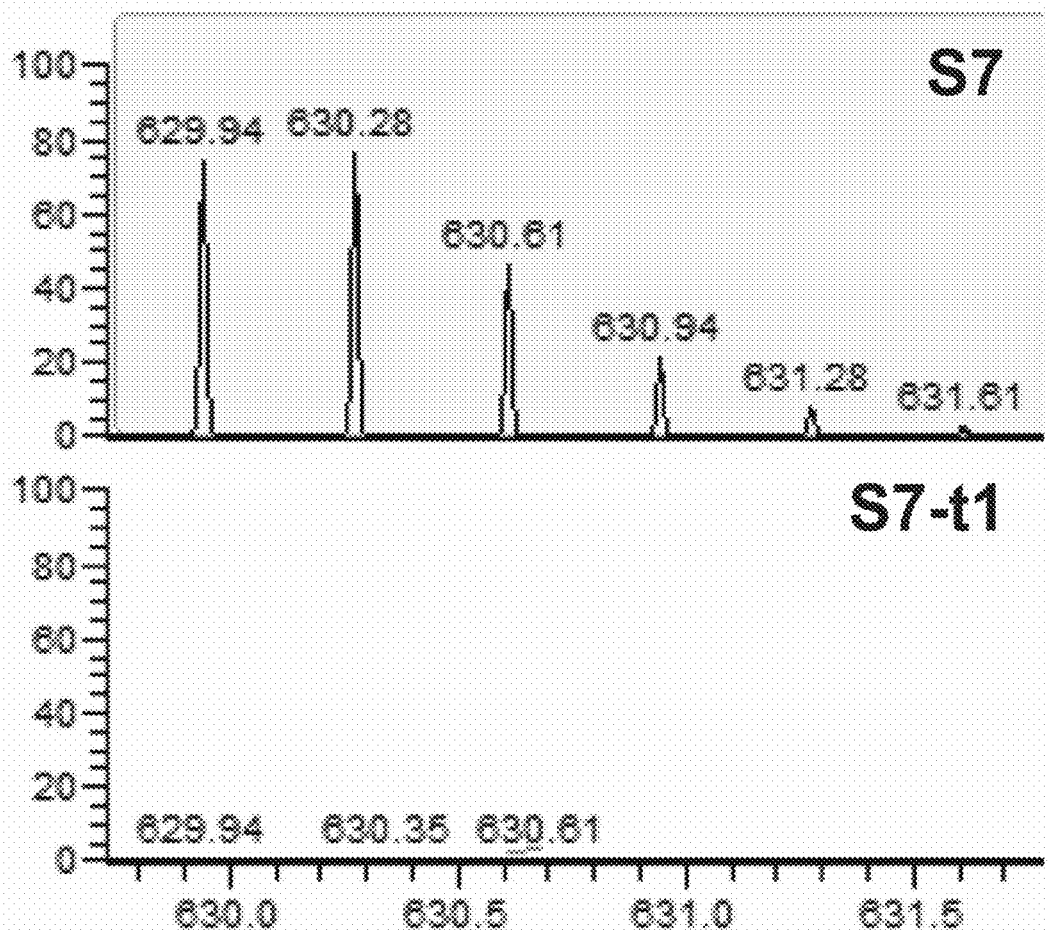
Fig. 8c

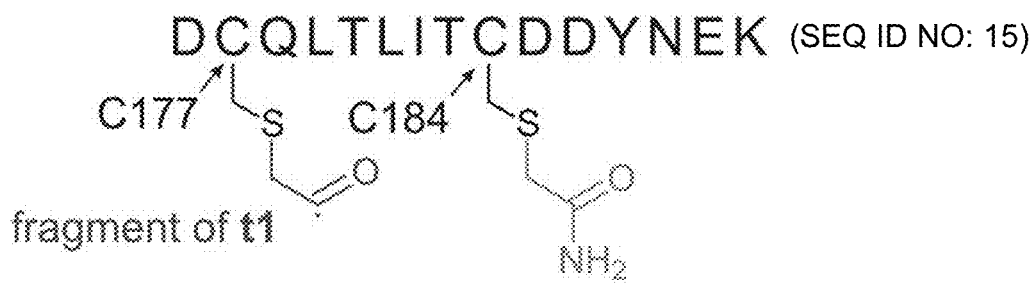
DCQLTLITCDDYNEK (SEQ ID NO: 15)
molecular formula (monoisotopic m):
$C_{77}H_{119}N_{18}O_{32}S_2$ (1871.77 g/mol)
calc. monoisotopic peak for $MH^{3+}$:
m/z = 936.89 th
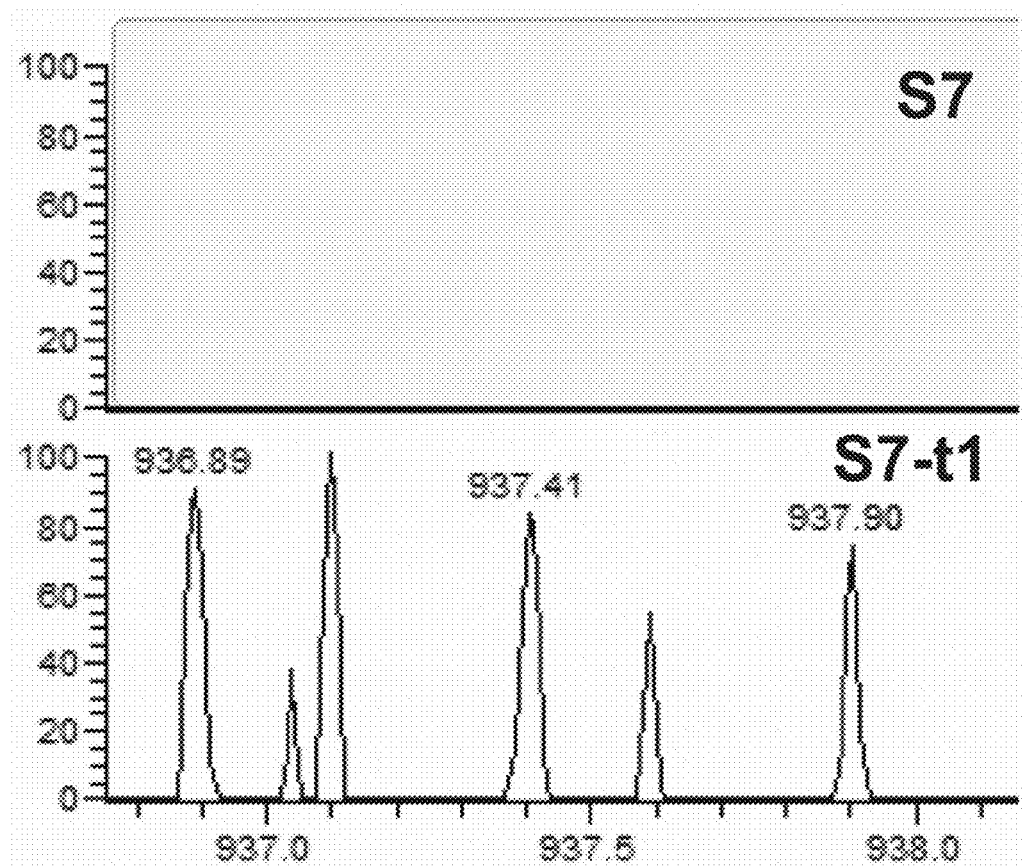
Fig. 8c, Cont'd

```
                10         20        30       40         50
         MDVFMKGLSK AKEGVVAAAE KTKQGVAEAA GKTKEGVLYV GSKTKEGVVH
                60         70        80       90        100
         GVATVAEKTK EQVTNVGGAV VTGVTAVQK  TVEGAGSIAA ATGFVKKDQL
               110        120       130      140        150
         GKNEEGAPQE GILEDMPVDP DNEAYEMPSE EGYQDYEPEA GGGGS

HHHHHH   (SEQ ID NO:2)
```

Fig. 9a

KIX wt:

```
      590        600        610        620        630
GVRKG WHEHVTQDLR SHLVHKLVQA IFPTPDPAAL KDRRMENLVA 640        650        660        670
YAKKVEGDMY ESANSRDEYY HLLAEKIYKI QKELEEKRRS R
```
(SEQ ID NO: 17)

```
      590        600        610        620        630
GVRKG WHEHVTQDLR SHLVHKLVQA IFPTPDPAAL KDRRMENLVA 640        650        660        670
YAKKVEGDMY ESANSRDEYY HLLAEKIYKI QKELEEKRRS R
```
(SEQ ID NO: 17)

Fig. 13b

| Variant | Mutation | Distance ($C_\alpha - C_\alpha$) |
|---|---|---|
| K1 | H594C-L599C-R646C | 10.0 Å |
|  | H594C-L599C-R646C | 11.5 Å |
|  | H594C-L599C-R646C | 7.8 Å |

Fig. 13c

| Variant | Mutation | Distance ($C_\alpha - C_\alpha$) |
|---|---|---|
| S7 | D111C-E149C-K177C | 12.4 Å |
|  | D111C-E149C-K177C | 15.7 Å |
|  | D111C-E149C-K177C | 8.5 Å |

Fig. 13d

| Ions | S7-t2 m/z calc. | m/z found |
|---|---|---|
| $[M+1H]^+$ | 17212.6 | - |
| $[M+9H]^{9+}$ | 1913.5 | 1913.3 |
| $[M+10H]^{10+}$ | 1722.3 | 1722.2 |
| $[M+11H]^{11+}$ | 1565.8 | 1565.5 |
| $[M+12H]^{12+}$ | 1435.4 | 1435.1 |
| $[M+13H]^{13+}$ | 1325.0 | 1324.8 |
| $[M+14H]^{14+}$ | 1230.5 | 1230.6 |
| $[M+14H]^{14+}$ | 1148.5 | 1148.5 |
| $[M+16H]^{16+}$ | 1076.8 | 1076.5 |
| $[M+17H]^{17+}$ | 1013.5 | 1013.3 |
| $[M+18H]^{18+}$ | 957.3 | 957.0 |

SEQUENCE LISTING

<160> NUMBER OF SEQ ID NOS: 18

<210> SEQ ID NO 1
<211> LENGTH: 150
<212> TYPE: PRT
<213> ORGANISM: Artificial Sequence
<220> FEATURE:
<223> OTHER INFORMATION: Srt A polypeptide

<400> SEQUENCE: 1

```
Gly Ser His Met Gln Ala Lys Pro Gln Ile Pro Lys Asp Lys Ser Lys
1               5                  10                  15

Val Ala Gly Tyr Ile Glu Ile Pro Asp Ala Asp Ile Lys Glu Pro Val
            20                  25                  30

Tyr Pro Gly Pro Ala Thr Pro Glu Gln Leu Asn Arg Gly Val Ser Phe
        35                  40                  45

Ala Glu Glu Asn Glu Ser Leu Asp Asp Gln Asn Ile Ser Ile Ala Gly
    50                  55                  60

His Thr Phe Ile Asp Arg Pro Asn Tyr Gln Phe Thr Asn Leu Lys Ala
65                  70                  75                  80

Ala Lys Lys Gly Ser Met Val Tyr Phe Lys Val Gly Asn Glu Thr Arg
                85                  90                  95

Lys Tyr Lys Met Thr Ser Ile Arg Asp Val Lys Pro Thr Asp Val Gly
            100                 105                 110

Val Leu Asp Glu Gln Lys Gly Lys Asp Lys Gln Leu Thr Leu Ile Thr
        115                 120                 125

Cys Asp Asp Tyr Asn Glu Lys Thr Gly Val Trp Glu Lys Arg Lys Ile
    130                 135                 140

Phe Val Ala Thr Glu Val
145                 150
```

<210> SEQ ID NO 2
<211> LENGTH: 156
<212> TYPE: PRT
<213> ORGANISM: Artificial Sequence
<220> FEATURE:
<223> OTHER INFORMATION: modified alpha-synuclein

<400> SEQUENCE: 2

```
Met Asp Val Phe Met Lys Gly Leu Ser Lys Ala Lys Glu Gly Val Val
1               5                  10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala Gly Gly Gly Gly
    130                 135                 140
```

```
Ser Leu Glu Pro Thr Gly His His His His His His
145                 150                 155
```

<210> SEQ ID NO 3
<211> LENGTH: 6
<212> TYPE: PRT
<213> ORGANISM: Artificial Sequence
<220> FEATURE:
<223> OTHER INFORMATION: hydrolysis product
<220> FEATURE:
<221> NAME/KEY: MISC_FEATURE
<222> LOCATION: (1)..(1)
<223> OTHER INFORMATION: coupled to Dabcyl

<400> SEQUENCE: 3

```
Gln Ala Leu Pro Glu Thr
1               5
```

<210> SEQ ID NO 4
<211> LENGTH: 4
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (4)..(4)
<223> OTHER INFORMATION: coupled to FITC

<400> SEQUENCE: 4

```
Gly Gly Gly Lys
1
```

<210> SEQ ID NO 5
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: coupled to Dabcyl
<220> FEATURE:
<221> NAME/KEY: MOD_RES
<222> LOCATION: (9)..(9)
<223> OTHER INFORMATION: coupled to FITC

<400> SEQUENCE: 5

```
Gln Ala Leu Pro Glu Thr Gly Glu Lys
1               5
```

<210> SEQ ID NO 6
<211> LENGTH: 16
<212> TYPE: PRT
<213> ORGANISM: Artificial Sequence
<220> FEATURE:
<223> OTHER INFORMATION: MLL derived peptide
<220> FEATURE:
<221> NAME/KEY: MOD_RES
<222> LOCATION: (1)..(1)
<223> OTHER INFORMATION: coupled to FITC-O2Oc
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (16)..(16)
<223> OTHER INFORMATION: AMIDATION

<400> SEQUENCE: 6

```
Gly Asn Ile Leu Pro Ser Asp Leu Asp Phe Val Leu Lys Asn Thr Pro
1               5                   10                  15

<210> SEQ ID NO 7
<211> LENGTH: 501
<212> TYPE: PRT
<213> ORGANISM: Bos taurus

<400> SEQUENCE: 7

Met Ser Ser Ser Ala Met Pro Asp Val Pro Ala Pro Leu Thr Asn Leu
1               5                   10                  15

Gln Phe Lys Tyr Thr Lys Ile Phe Ile Asn Asn Glu Trp His Ser Ser
                20                  25                  30

Val Ser Gly Lys Lys Phe Pro Val Phe Asn Pro Ala Thr Glu Glu Lys
            35                  40                  45

Leu Cys Glu Val Glu Glu Gly Asp Lys Glu Asp Val Asp Lys Ala Val
        50                  55                  60

Lys Ala Ala Arg Gln Ala Phe Gln Ile Gly Ser Pro Trp Arg Thr Met
65                  70                  75                  80

Asp Ala Ser Glu Arg Gly Arg Leu Leu Asn Lys Leu Ala Asp Leu Ile
                85                  90                  95

Glu Arg Asp His Leu Leu Leu Ala Thr Met Glu Ala Met Asn Gly Gly
                100                 105                 110

Lys Leu Phe Ser Asn Ala Tyr Leu Met Asp Leu Gly Gly Cys Ile Lys
            115                 120                 125

Thr Leu Arg Tyr Cys Ala Gly Trp Ala Asp Lys Ile Gln Gly Arg Thr
130                 135                 140

Ile Pro Met Asp Gly Asn Phe Phe Thr Tyr Thr Arg Ser Glu Pro Val
145                 150                 155                 160

Gly Val Cys Gly Gln Ile Ile Pro Trp Asn Phe Pro Leu Leu Met Phe
                165                 170                 175

Leu Trp Lys Ile Gly Pro Ala Leu Ser Cys Gly Asn Thr Val Val Val
                180                 185                 190

Lys Pro Ala Glu Gln Thr Pro Leu Thr Ala Leu His Met Gly Ser Leu
            195                 200                 205

Ile Lys Glu Ala Gly Phe Pro Pro Gly Val Val Asn Ile Val Pro Gly
        210                 215                 220

Tyr Gly Pro Thr Ala Gly Ala Ala Ile Ser Ser His Met Asp Val Asp
225                 230                 235                 240

Lys Val Ala Phe Thr Gly Ser Thr Glu Val Gly Lys Leu Ile Lys Glu
                245                 250                 255

Ala Ala Gly Lys Ser Asn Leu Lys Arg Val Ser Leu Glu Leu Gly Gly
                260                 265                 270

Lys Ser Pro Cys Ile Val Phe Ala Asp Ala Asp Leu Asp Asn Ala Val
            275                 280                 285

Glu Phe Ala His Gln Gly Val Phe Tyr His Gln Gly Gln Cys Cys Ile
        290                 295                 300

Ala Ala Ser Arg Leu Phe Val Glu Ser Ile Tyr Asp Glu Phe Val
305                 310                 315                 320

Arg Arg Ser Val Glu Arg Ala Lys Lys Tyr Val Leu Gly Asn Pro Leu
                325                 330                 335

Thr Pro Gly Val Ser Gln Gly Pro Gln Ile Asp Lys Glu Gln Tyr Glu
            340                 345                 350

Lys Ile Leu Asp Leu Ile Glu Ser Gly Lys Lys Glu Gly Ala Lys Leu
```

```
                    355                 360                 365
Glu Cys Gly Gly Gly Pro Trp Gly Asn Lys Gly Tyr Phe Ile Gln Pro
            370                 375                 380
Thr Val Phe Ser Asp Val Thr Asp Asp Met Arg Ile Ala Lys Glu Glu
385                 390                 395                 400
Ile Phe Gly Pro Val Gln Gln Ile Met Lys Phe Lys Ser Leu Asp Asp
                405                 410                 415
Val Ile Lys Arg Ala Asn Asn Thr Phe Tyr Gly Leu Ser Ala Gly Ile
            420                 425                 430
Phe Thr Asn Asp Ile Asp Lys Ala Ile Thr Val Ser Ser Ala Leu Gln
            435                 440                 445
Ser Gly Thr Val Trp Val Asn Cys Tyr Ser Val Val Ser Ala Gln Cys
        450                 455                 460
Pro Phe Gly Gly Phe Lys Met Ser Gly Asn Gly Arg Glu Leu Gly Glu
465                 470                 475                 480
Tyr Gly Phe His Glu Tyr Thr Glu Val Lys Thr Val Thr Ile Lys Ile
                485                 490                 495
Ser Gln Lys Asn Ser
            500

<210> SEQ ID NO 8
<211> LENGTH: 4
<212> TYPE: PRT
<213> ORGANISM: Artificial Sequence
<220> FEATURE:
<223> OTHER INFORMATION: tag

<400> SEQUENCE: 8

Leu Pro Glu Thr
1

<210> SEQ ID NO 9
<211> LENGTH: 5
<212> TYPE: PRT
<213> ORGANISM: Artificial Sequence
<220> FEATURE:
<223> OTHER INFORMATION: tag

<400> SEQUENCE: 9

Leu Pro Glu Thr Gly
1               5

<210> SEQ ID NO 10
<211> LENGTH: 7
<212> TYPE: PRT
<213> ORGANISM: Artificial Sequence
<220> FEATURE:
<223> OTHER INFORMATION: tag

<400> SEQUENCE: 10

Leu Pro Glu Thr Gly Gly Gly
1               5

<210> SEQ ID NO 11
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: coupled to Dabcyl
```

-continued

```
<400> SEQUENCE: 11

Gln Ala Leu Pro Glu Thr Gly Gly Gly
1               5

<210> SEQ ID NO 12
<211> LENGTH: 151
<212> TYPE: PRT
<213> ORGANISM: Artificial Sequence
<220> FEATURE:
<223> OTHER INFORMATION: Srt A polypeptide

<400> SEQUENCE: 12

Gly Ser His Met Gln Ala Lys Pro Gln Ile Pro Lys Asp Lys Ser Lys
1               5                   10                  15

Val Ala Gly Tyr Ile Glu Ile Pro Asp Ala Asp Ile Lys Glu Pro Val
                20                  25                  30

Tyr Pro Gly Pro Ala Thr Pro Glu Gln Leu Asn Arg Gly Val Ser Phe
            35                  40                  45

Ala Glu Glu Asn Glu Ser Leu Asp Asp Gln Asn Ile Ser Ile Ala Gly
        50                  55                  60

His Thr Phe Ile Asp Arg Pro Asn Tyr Gln Phe Thr Asn Leu Lys Ala
65                  70                  75                  80

Ala Lys Lys Gly Ser Met Val Tyr Phe Lys Val Gly Asn Glu Thr Arg
                85                  90                  95

Lys Tyr Lys Met Thr Ser Ile Arg Asp Val Lys Pro Thr Asp Val Gly
            100                 105                 110

Val Leu Asp Glu Gln Lys Gly Lys Asp Lys Gln Leu Thr Leu Ile Thr
        115                 120                 125

Cys Asp Asp Tyr Asn Glu Lys Thr Gly Val Trp Glu Lys Arg Lys Ile
    130                 135                 140

Phe Val Ala Thr Glu Val Lys
145                 150

<210> SEQ ID NO 13
<211> LENGTH: 35
<212> TYPE: PRT
<213> ORGANISM: Artificial Sequence
<220> FEATURE:
<223> OTHER INFORMATION: part of Srt A peptide
<220> FEATURE:
<221> NAME/KEY: MOD_RES
<222> LOCATION: (12)..(12)
<223> OTHER INFORMATION: modified cysteine

<400> SEQUENCE: 13

Gly Val Ser Phe Ala Glu Glu Asn Glu Ser Leu Cys Asp Gln Asn Ile
1               5                   10                  15

Ser Ile Ala Gly His Thr Phe Ile Asp Arg Pro Asn Tyr Gln Phe Thr
                20                  25                  30

Asn Leu Lys
        35

<210> SEQ ID NO 14
<211> LENGTH: 14
<212> TYPE: PRT
<213> ORGANISM: Artificial Sequence
<220> FEATURE:
<223> OTHER INFORMATION: part of Srt A peptide
<220> FEATURE:
<221> NAME/KEY: MOD_RES
<222> LOCATION: (12)..(12)
```

```
<223> OTHER INFORMATION: modified cysteine

<400> SEQUENCE: 14

Lys Gly Ser Met Val Tyr Phe Lys Val Gly Asn Cys Thr Arg
1               5                   10

<210> SEQ ID NO 15
<211> LENGTH: 15
<212> TYPE: PRT
<213> ORGANISM: Artificial Sequence
<220> FEATURE:
<223> OTHER INFORMATION: part of Srt A peptide
<220> FEATURE:
<221> NAME/KEY: MOD_RES
<222> LOCATION: (2)..(2)
<223> OTHER INFORMATION: modified cysteine
<220> FEATURE:
<221> NAME/KEY: MOD_RES
<222> LOCATION: (9)..(9)
<223> OTHER INFORMATION: modified cysteine

<400> SEQUENCE: 15

Asp Cys Gln Leu Thr Leu Ile Thr Cys Asp Asp Tyr Asn Glu Lys
1               5                   10                  15

<210> SEQ ID NO 16
<211> LENGTH: 156
<212> TYPE: PRT
<213> ORGANISM: Artificial Sequence
<220> FEATURE:
<223> OTHER INFORMATION: modified alpha-synuclein
<220> FEATURE:
<221> NAME/KEY: SITE
<222> LOCATION: (141)..(145)
<223> OTHER INFORMATION: flexible linker
<220> FEATURE:
<221> NAME/KEY: SIGNAL
<222> LOCATION: (146)..(150)
<223> OTHER INFORMATION: sorting signal
<220> FEATURE:
<221> NAME/KEY: BINDING
<222> LOCATION: (151)..(156)
<223> OTHER INFORMATION: His-tag

<400> SEQUENCE: 16

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala Gly Gly Gly Gly
    130                 135                 140

Ser Leu Glu Pro Thr Gly His His His His His His
145                 150                 155
```

```
<210> SEQ ID NO 17
<211> LENGTH: 86
<212> TYPE: PRT
<213> ORGANISM: Homo sapiens

<400> SEQUENCE: 17

Gly Val Arg Lys Gly Trp His Glu His Val Thr Gln Asp Leu Arg Ser
1               5                   10                  15

His Leu Val His Lys Leu Val Gln Ala Ile Phe Pro Thr Pro Asp Pro
            20                  25                  30

Ala Ala Leu Lys Asp Arg Arg Met Glu Asn Leu Val Ala Tyr Ala Lys
        35                  40                  45

Lys Val Glu Gly Asp Met Tyr Glu Ser Ala Asn Ser Arg Asp Glu Tyr
    50                  55                  60

Tyr His Leu Leu Ala Glu Lys Ile Tyr Lys Ile Gln Lys Glu Leu Glu
65                  70                  75                  80

Glu Lys Arg Arg Ser Arg
                85

<210> SEQ ID NO 18
<211> LENGTH: 86
<212> TYPE: PRT
<213> ORGANISM: Artificial Sequence
<220> FEATURE:
<223> OTHER INFORMATION: KIX variant

<400> SEQUENCE: 18

Gly Val Arg Lys Gly Trp His Glu Cys Val Thr Gln Asp Cys Arg Ser
1               5                   10                  15

His Leu Val His Lys Leu Val Gln Ala Ile Phe Pro Thr Pro Asp Pro
            20                  25                  30

Ala Ala Leu Lys Asp Arg Arg Met Glu Asn Leu Val Ala Tyr Ala Lys
        35                  40                  45

Lys Val Glu Gly Asp Met Tyr Glu Ser Ala Asn Ser Cys Asp Glu Tyr
    50                  55                  60

Tyr His Leu Leu Ala Glu Lys Ile Tyr Lys Ile Gln Lys Glu Leu Glu
65                  70                  75                  80

Glu Lys Arg Arg Ser Arg
                85
```

PROTEIN MACROCYCLIZATION

RELATED APPLICATIONS

This application is a National Stage Application under 35 U.S.C. 371 of co-pending PCT application PCT/NL2019/050229 designating the United States and filed Apr. 18, 2019; which claims the benefit of EP application number 18168298.0 and filed Apr. 19, 2018 each of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Mar. 28, 2023, is named P118365US00 seqlist_ST25.txt and is 15,248 bytes in size.

FIELD OF THE INVENTION

The present invention relates to methods and trivalent thiol-reactive cross-linkers for the macrocyclization of proteins. The invention is useful for increasing the stability of a protein.

BACKGROUND OF THE INVENTION

Enzymes are an essential component of most biotechnological and biomedical processes[1,2] but their scope of application is hampered by a limited stability under often desired harsh conditions (e.g. elevated temperature or presence of denaturants). Consequently, the stabilization of protein structures is a central aspect in the development of suitable enzymes. The complexity of interactions in protein tertiary structures and the sensitivity of enzymatic activity on sequence alterations render enzyme stabilization very challenging. A minimal invasive strategy involves the use of covalent protein modifications (e.g. pegylation or glycosylation) being mainly applied to increase biostability for therapeutic applications.[3,4] Alternatively, enzyme stabilization can be achieved via alterations in the protein sequence applying directed evaluation, consensus-based mutagenesis or computational approaches[5,6,7,8] which can be complimented by the introduction of non-proteinogenic amino acids.[9] These approaches aim for improved protein core interactions, structure rigidification, and/or surface charge distribution and often require multiple rounds of optimization to achieve relevant stabilization effects.

There exists a need for new methods to increase the stability of proteins, in particular enzymes.

SUMMARY OF THE INVENTION

In one aspect the disclosure provides a method for increasing the stability of a protein, wherein the protein comprises at least 70 amino acids, said method comprising:
a) providing a protein comprising three cysteine residues and
b) contacting said protein with a trivalent thiol-reactive cross-linker such that the linker forms covalent bonds with each of the three cysteine residues.

Preferably, step a) comprises modifying a protein to introduce one or more of the three cysteine residues. Preferably, said protein comprises at least a fourth cysteine residue and wherein said method does not result in the formation of a covalent bond between the fourth cysteine and the cross-linker. Preferably, the protein is an enzyme and the fourth cysteine is part of the enzymatic active site. Preferably, the cross-linker has $C_3$ symmetry.

Preferably, the cross-linker has formula (I):

wherein
Q is a core structure selected from the group consisting of

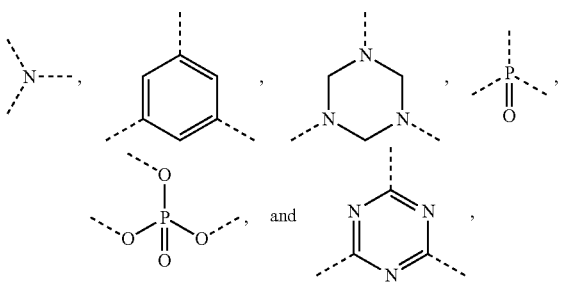

each dashed line in Q indicating a site where Q is bound to L,
each L is a linker independently selected from the group consisting of

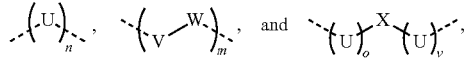

wherein
each U is independently selected from $CH_2$ and $CF_2$,
V is $CH_2$
W is $CF_2$
X is NR, NH or O,
wherein R is a fluorophore or affinity handle,
n is an integer in the range of 2-8,
m is an integer in the range of 1-4
is 2 or 3, and
v is 2 or 3,
each dashed line in L indicating a site where L is bound to Q or E,
each E is an electrophile independently selected from the group consisting of

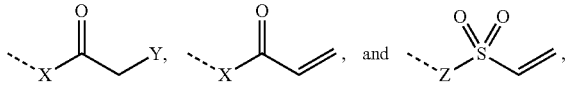

wherein
each X is independently selected from NH and O,
Y is selected from F, Cl, Br, Tos (O—$SO_2$—$C_6H_4$—$CH_3$), and Mes (O—$SO_2$—$CH_3$),
Z is $CH_2$, NH—C(O)—$CH_2$, or O—C(O)—$CH_2$
each dashed line in E indicating a site where E is bound to L.

The disclosure further provides a stabilized protein obtainable by a method as disclosed herein. Preferably the protein is a Sortase A polypeptide or a KIX domain polypeptide.

The disclosure further provides a trivalent thiol-reactive cross-linker having formula II:

wherein
Q is

each dashed line in Q indicating a site where Q is bound to L,
each L is a linker independently selected from the group consisting of

wherein
each U is independently selected from $CH_2$ and $CF_2$,
V is $CH_2$
W is $CF_2$
X is NR, NH or O,
wherein R is a fluorophore or affinity handle, n is an integer in the range of 2-8,
m is an integer in the range of 1-4
is 2 or 3, and
v is 2 or 3,
each dashed line in L indicating a site where L is bound to Q or E,
each E is an electrophile independently selected from the group consisting of

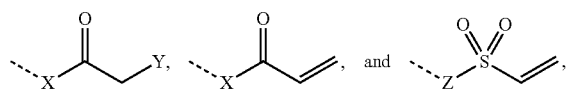

wherein
each X is independently selected from NH and O,
Y is selected from F, Cl, Br, Tos ($O-SO_2-C_6H_4-CH_3$), and Mes ($O-SO_2-CH_3$),
Z is $CH_2$, $NH-C(O)-CH_2$, or $O-C(O)-CH_2$
each dashed line in E indicating a site where E is bound to L.
Preferably,
L is

U is $CH_2$, preferably n is 2 or 3; and

E is

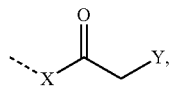

wherein X is NH and Y is F, Cl, or Br, preferably Cl.
Preferably the cross-linker is Formula III:

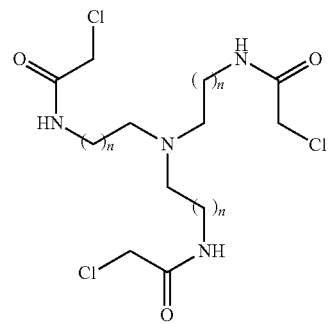

wherein n is 1 or n is 2.

The disclosure further provides the use of the cross-linkers disclosed herein for reacting with thiol groups, preferably for cross-linking three cysteine resides present in a protein.

The disclosure further provides a protein comprising at least 70 amino acids and comprising at least three cysteine residues, wherein each of the three cysteine residues is covalently bonded to a trivalent thiol-reactive cross-linker. Preferably, the trivalent thiol-reactive cross-linker is a cross-linker as disclosed herein.

The disclosure further provides a Sortase A polypeptide comprising amino acid substitutions with cysteine at positions 111, 149, and 177, with reference to amino acid position numbering of *Staphylococcus aureus* SrtA, preferably wherein the polypeptide has SEQ ID NO: 1.

The disclosure further provides a KIX domain polypeptide comprising amino acid substitutions with cysteine at positions 594, 599, and 646, with reference to amino acid position numbering of FIG. 13b, preferably wherein the polypeptide has the sequence depicted in FIG. 13c.

BRIEF DESCRIPTION OF THE DRAWINGS

FIG. 4. a) HPLC chromatograms (440 nm) of transpeptidation reaction (12 h at 65° C.) with fluorescence probe (●) in absence of enzyme (light grey), with SrtA (dark grey) or with S7-t1 (red). Product formation (▲, ■) was only observed in presence of S7-t1 (50 μM enzyme, 10 μM probe, 2.5 mM GGG); b) Temperature dependence of enzymatic activity ($v_r$, relative to SrtA at 37° C.) (10 μM enzyme, 10 μM probe, 2.5 mM GGG, buffer: 20 mM HEPES, pH 7.5, 150 mM NaCl, 5 mM CaCl2), 2 mM TCEP, 0.01% TWEEN). Values are mean of triplicate (+/−1 σ, * p<0.05,  p<0.01, * p<0.001, ns: not significant); c) Relative enzymatic activity ($v_r$, relative to SrtA in absence of GdnHCl) at 37° C. for various concentrations of GdnHCl (for conditions and data processing see 3b); d) Coomassie-stained SDS-PAGE gel showing the soluble α-Syn fractions before fibril formation (A) and after re-solubilization in absence (B) and presence (C) of GdnHCl (1 M); e) Fluorescent readout ($\lambda_{em}$=520 nm) of α Syn labeling using soluble fractions before fibril formation A (w/o GdnHCl) and after re-solubilization B (w/o GdnHCl) and C (1 M GdnHCl) with either SrtA or S7-t1.

FIG. 6: a) Amino acid sequence of SrtA cloned, expressed and evaluated in the present study; b) List of StrA variants (highlighted in the corresponding color code (see FIG. 2b)) and measured distances between Ca atoms in the NMR structure (PDB code: 1ija).

FIG. 13: a) Amino acid sequence of KIX wt sub-cloned, expressed and evaluated in the present study. b) Amino acid sequence of KIX variant K1 sub-cloned, expressed and evaluated in the present study. Mutations are highlighted in green. SEQ ID NO: 18. c) Averaged distance between the Ca atoms of underlined amino acid positions over the 20 conformers of the KIX NMR structure (PDB code: 2agh). d) Cysteine positions in S7 variant. Averaged distance between the Ca atoms of underlined amino acid positions over the 25 conformers of the SrtA NMR structure (PDB code: 1ija).

DETAILED DESCRIPTION OF THE DISCLOSED EMBODIMENTS

Figure 1A:
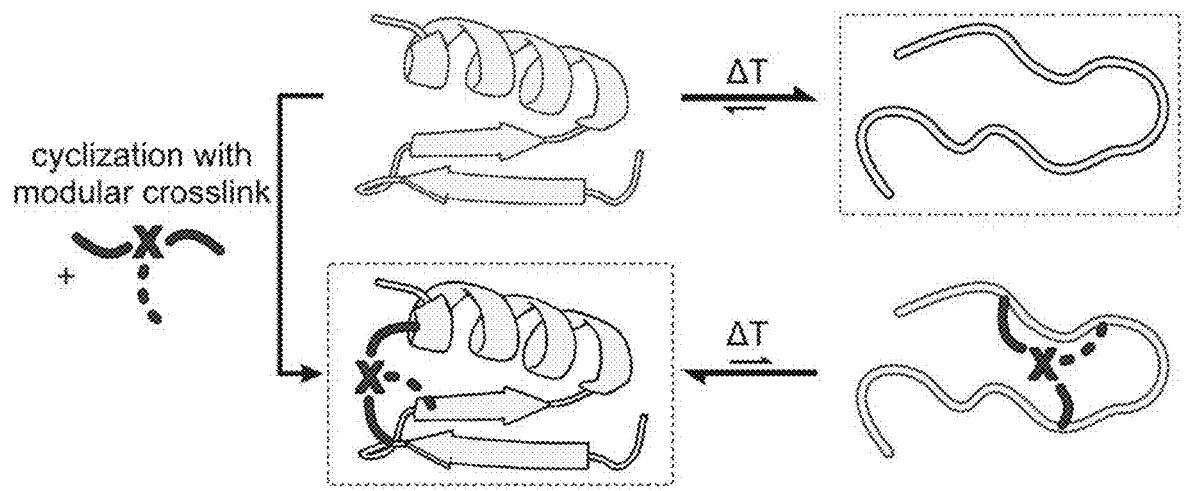
FIG. 1. a) Macrocyclization strategy towards stabilized protein tertiary structures using a modular bis- or triselectrophilic crosslink; b) Electrophiles (maleimide 1,2-bromoacetamide 2,2-chloroacetamide 3, acrylamide 4) considered for crosslinking of accessible cysteines.

Increasing the stabilization of enzymes against denaturants and elevated temperature has also been studied by the introduction of intramolecular crosslinks. There have been reports of the installation of additional disulfide bridges or, as recently reported for non-enzymatic protein domains, the introduction of disulfide mimics[10] which are insensitive to reducing environments. In addition, the crosslinking of protein termini via lactam formation was applied[11-13] requiring a suitable spatial alignment of N- and C-terminus in the tertiary structure.

To reduce these structural prerequisites, the incorporation of non-natural electrophilic amino acids was pursued to enable crosslinking with appropriately aligned cysteine side chains.[14] However, the use of amber stop codon suppression for the introduction of these non-natural amino acids complicates protein expression. In addition, the screening of linker libraries is hampered since incorporation of these modified amino acids requires adapted tRNA synthetases which is work intensive and does not succeed for every non-natural amino acid.[15] As such, cross-linking approaches that rely on the use of non-natural amino acids suffer a number of disadvantages.

The present disclosure provides methods for producing cross-linked proteins that do not rely on the use of non-natural amino acids. The protein may have any function, e.g., cytokines, chemokines, growth factors, hormones, antibodies, receptors, and antigens, etc. In some embodiments, the protein is an enzyme. As is apparent to a skilled person, the cross-linked proteins described herein include proteins composed of more than one polypeptide or peptide chain. For example, antibodies are an exemplary protein of the disclosure and IgG antibodies are made up of four peptide chains. Receptors are also exemplary proteins of the disclosure and many proteins are made up of, e.g., hetero- or homo-dimers. In some embodiments, the cysteine residues are present in different polypeptides or peptide chains, such that the cross-links are formed between polypeptide/peptide chains. For example, the present disclosure contemplates methods for increasing the stability of a hetero-dimer receptor. As an example of one of the many embodiments contemplated herein, a hetero-dimer receptor is provided having one cysteine residue in one receptor subunit and two cysteine residues in the other receptor subunit such that when the receptor is contacted with a trivalent thiol-reactive cross-linker the linker forms covalent bonds with each of the three cysteine residues and between the dimers.

In particular, the methods improve the stability of a protein using cross-linking reagents. As is clear to a skilled person, an increase in stability refers to an increase in stability of the cross-linked protein as compared to the stability of the protein without cross-linking. The term "increased stability" as used herein, refers to—an increase in resistance to—or—a decrease in susceptibility to—denaturation. Denaturation refers to the loss of secondary or tertiary structure and the biological function, in particular enzymatic activity, of most proteins is reduced or lost when denatured. Denaturation can occur as a result of mechanical agitation, radiation, increased temperature, or by chemical denaturants. In some embodiments, improved stability refers to the presence of a higher ratio of folded to unfolded protein when cross-linked, relative to that of the protein without cross-linking. Improved stability can be determined by examining the amount of folded protein present under varying conditions, e.g., temperature, detergent, denaturing agents, and pH. In preferred embodiments, the methods improve the thermal stability and/or stability against chemical denaturants.

In some embodiments, the stability of the protein can be determined by measuring the Tm. The term "Tm" refers to the temperature at which 50% of the protein has unfolded. Typically, the higher the Tm, the more stable the protein. In some embodiments, the methods are for increasing the Tm of a protein.

In some embodiments, the stability of the protein can be determined by measuring the effects of chemical agents on the protein. Chemical denaturants are agents that can disrupt non-covalent interactions and covalent bonds within a protein. Exemplary chemical denaturants include guanidinium hydrochloride, guanadinium thiocyanate, urea, acetone, organic solvents, salts, reducing agents (e.g. dithiothreitol, beta-mercaptoethanol, dinitrothiobenzene), detergents, and acids. Biological agents, such as proteases, may also act as denaturants.

In some embodiments, the methods comprise
a) providing a protein (I) comprising three cysteine residues as disclosed herein and
b) contacting said protein with a trivalent thiol-reactive cross-linker as disclosed herein such that the linker forms covalent bonds with each of the three cysteine residues resulting in a cross-linked protein (II), wherein the cross-linked protein (II) has an increased Tm and/or an increased resistance to denaturation as compared to the protein lacking crosslinking (I).

The methods disclosed herein comprise providing a protein which comprises three cysteine residues. The protein is contacted with a trivalent thiol-reactive cross-linker such that the linker forms covalent bonds with each of the three cysteine residues. As described in the examples, bicyclization resulted in a stronger stabilization of protein tertiary structure compared to monocyclization, while still retaining protein function. In some embodiments, the three cysteine residues which are cross-linked are endogenous to the protein. However, for most proteins one or more of the three cysteine residues will be introduced into the protein. The introduction of cysteine residues may be accomplished by any method known to a skilled person, e.g, by chemically synthesizing the modified protein or by introducing the one or more cysteines using recombinant DNA technology. In some embodiments, modified proteins can be cloned in expression vectors and expressed in cell culture by techniques well-known in the art. It is also apparent that the disclosure encompasses proteins having more than one of the linkages described herein. For example, a protein may be provided with six cysteine residues, wherein three of the cysteine residues are able to be cross-linked while the other three cysteine residues are able to be cross-linked. In such embodiments, the cross-linker may be the same or different for each set of three cysteine residues.

Short peptides generally do not retain their native conformation. In fact, many peptides are extremely flexible. Thus peptide stapling techniques have been developed as a mean to constrain short peptides in a particular conformation and reduce backbone flexibility (reviewed in, e.g., Lau et al. 2015 Chem Soc Rev 44:91-102). It is also useful in drug discovery to constrain short linear peptides in order to adopt new structures with novel activities. For example, Bashiruddin et al. (2015 Bioorganic Chemistry 61: 45-50) describes a method of ribosomally synthesizing fused tricyclic peptides. The technology is used for generating libraries of ° peptides having new structures which can then be used, for example, in screening for bioactivity in particular to identify new functions. In this method, peptides are translated with an N-terminal ClAc group, one Cys residue at the second position and three more arbitrarily spaced downstream Cys residues, followed by the addition of TBMB. Bashiruddin et al. only tests short peptides having a length of less than 40 amino acids.

Chen et al. (2012 ChemBioChem 13: 1032-1038) is also concerned with peptide libraries for screening for high-affinity ligands. A 17-amino acid peptide was completely reduced with TCEP and incubated with different linker compounds dissolved in acetonitrile (an organic solvent). The authors conclude that combining different linkers with random peptide libraries could be a strategy for generating libraries of structurally highly diverse macrocyclic proteins.

Unlike peptide stapling which structurally reinforces a short string of amino acids in a particular secondary structure or loop conformation, the presently disclosed methods improve the stability of a protein tertiary structure. The disclosure concerns proteins having at least 70 amino acids. In some embodiments, the proteins have at least 80 amino acids or even at least 100 amino acids. Unlike the simple structure of a peptide, the multiple secondary structures of a protein fold to form a more complex three-dimensional structure. Preferably, the methods relate to proteins having at least two distinct secondary structures. Preferably, the protein provided in the method is a folded protein or rather a protein that has not been denatured before cross-linking. As explained herein, one of the objects of the present disclosure is to provide methods which stabilize the 'natural' folding or structure of a protein. In preferred embodiments, the methods increase the stability of the (natural) tertiary structure of a protein as compared to the non-cross-linked protein.

As used herein, "secondary structure" of a protein are defined by the patterns of hydrogen bonds between backbone amino and carboxyl groups. Alpha helices, beta sheets, beta turns and omega loops are exemplary secondary structures in proteins. As used herein, "tertiary structure" refers to the three dimensional shape of a protein.

Protein structure prediction techniques are well-known in the art and include homology modeling and threading, as well as more advanced methods that utilize neural networks, hidden Markov models and support vector machines. In addition, the tertiary structure of a protein can be determined by known-methods such as X-ray crystallography or nuclear magnetic resonance (NMR) studies. Publicly available software such as the Rosetta software can also be used for proteins structure prediction and to design new structures. See Voet, Pratt, Voet: Principles of Biochemistry, 2017 Chapter 6 Proteins: Three-Dimensional Structure for a review on protein folding and secondary structure; structure prediction and determining protein structure.

Preferably, the three cysteines for cross-linking are located in at least two distinct secondary structures. For example, the first cysteine may be located in a first alpha helix and the second cysteine may be located in a second alpha helix. The third cysteine may be located in either the first or second alpha helix or in a further secondary structure. Such methods have the advantage that the cross-linking increases the stability between at least two secondary structures. More preferably, the three cysteines for cross-linking are located in at least three distinct secondary structures.

The three cysteine residues are suitably located within the protein so that the cross-linker disclosed herein can form covalent bonds with each of the three cysteine residues. Preferably, the cysteine residues are separated in the primary amino acid sequence by at least 3 amino acids, while still being in spacial proximity. Preferably, the alpha-C atoms of the three cysteine residues form a triangle with side lengths between 6 to 23 Angstrom. Preferably, the cysteines are facing the same side of the protein.

Design principles known in the art of peptide stapling may be considered when introducing one or more cysteine residues into the protein for cross-linking. For example, it is known that amino acid residues of a peptide which lie on the same face of an alpha helix can be covalently joined or "stapled". The spacing of such residues is generally, i,i+4, i+7, i+11, i+12, i+14 and i+15. In order to promote the stability of a beta-sheet, the spacing of residues to be stapled is generally, i, i,i+2, i+4, i+6, i+8, i+10, etc. The staple imparts rigidity, and reinforces the desired secondary structure of the peptide.

It is preferred that the preferred positions for the three cysteine residues are not buried or core positions. "Buried position" as used herein refers to positions that are in the interior of a protein and/or which are inaccessible or nearly inaccessible to solvent. The accessible surface area of a protein can be determined by a number of different prediction methods (see, e.g., Zheng, et al, Proteins: Structure, Function, and Bioinformatics. 2004; 57:558-564; and Faraggi et al., Proteins. 2014 November; 82(11): 3170-3176). Preferably, the three cysteine residues are located on the surface of the tertiary structure and are not involved in binding (e.g., ligand binding, substrate recognition).

In some embodiments, the protein comprises at least a fourth cysteine residue, which is not cross-linked as a result of the method. Such methods are particularly useful when the protein comprises a cysteine residue that has a biological role, e.g., in a binding domain or enzymatic active site. As described in the examples, application of the present methods to a modified SrtA polypeptide surprisingly resulted in the cross-linking of three recombinantly introduced cysteine residues, while an endogenous cysteine residue which is crucial for enzymatic activity was not cross-linked.

One of the advantages of the methods disclosed herein is that the cross-linking does not rely on non-naturally occurring amino acids. In some embodiments, the protein does not comprise non-naturally occurring amino acids. The term "non-naturally occurring amino acid" includes amino acids that are different from naturally occurring amino acids in their side chain functionality. Naturally occurring amino acids include the 20 common amino acids: alanine, arginine, glycine, asparagine, aspartic acid, cysteine, glutamine, glutamic acid, serine, threonine, histidine, lysine, methionine, proline, valine, isoleucine, leucine, tyrosine, tryptophan, phenylalanine; as well as pyrolysine and selenocysteine.

In embodiments where non-endogenous cysteine residues are introduced into the protein, the effects of the modifications can be determined in, e.g., biological activity assays. For example, if the protein is an enzyme, the enzymatic activity of the protein having one or more cysteines introduced can be measured. While some loss of enzymatic activity is acceptable, modifications which significantly reduce enzymatic activity should be avoided. Similar assays can be performed to determine the effects of e.g., binding (e.g., affinity and specificity) and protein activity (e.g., downstream signaling). In vitro screening methods to measure the biological activity of proteins are well-known.

The present disclosure relates to trivalent thiol-reactive cross-linkers for increasing protein stability, as disclosed herein. As used herein, the term "cross-linker" refers to a reagent capable of chemically linking molecules, for example proteins, by one or more covalent bonds. The crosslinking reagents are "trivalent thiol-reactive", i.e., they contain three reactive ends that are capable of attaching to a sulfhydryl group, e.g., a thiol side chain in cysteine. Preferably, the thiol-reactive end of the cross-linker comprises an electrophile. Preferably, the cross-linker is homo-trifunctional, or rather each thiol reactive end has the same functional group. Preferably, the cross-linker has a C3-symmetric core. This has the advantage that only one form of (tri)cross-linked protein will be formed. Trivalent thiol-reactive cross-linkers are known in the art (see, e.g., 26-29). However, such cross-linkers have not been described for being able to increase the stability of proteins having at least 70 amino acids, while maintaining protein function (in particular binding activity or enzymatic function).

In some embodiments, the trivalent thiol-reactive cross-linker comprises a fluorophore or an affinity handle. Suitable fluorophores are well-known in the art and include Alexa Fluor 350, Alexa Fluor 405, AMCA, Marina Blue dye, and Cascade Blue dye (available from Invitrogen). Affinity handles refers to molecules that can be used for detection and/or purification. Suitable affinity handles are known in the art and may include an antibody, a double-stranded DNA sequence, modified nucleic acids and nucleic acid mimics such as peptide nucleic acids, locked nucleic acids, phosphorodiamidate morpholino oligomers (PMO), a ligand, a receptor, a peptide, or a small molecule for which a cognate binding agent is readily available. Suitable affinity tags are peptide 'tags' such as polyhistidine, Calmodulin, S-tag, SBP-tag, Strep-tag, V5, FLAG, HA and Myc tags. Other suitable affinity tags are well-known in the art.

The cross-linking reaction is carried out under conditions known in the art. See, e.g., Mattson et al. Molecular Biology Reports 1993, Volume 17: pp 167-183; Paramelle et al. Proteomics 2013 13:438-456. In general, the reaction is carried out at a pH between 6-8 and at a temperature of between 4-40° C. Optionally, the efficiency and/or specificity of the cross-linking reaction can be determine, e.g., using MS. As described further herein, one of the objects of the present disclosure is to provide methods which stabilize the 'natural' folding or structure of a protein. Preferably, the reaction is carried out under conditions which do not disrupt the tertiary structure of the protein.

Some cross-linkers require organic solvents for solubility. The presence of organic solvents may lead to the denaturation of the protein. In preferred embodiments, the reaction is carried out without the use of organic solvents. Preferred cross-linkers are those which do not require organic solvents for solubility.

In some embodiments, the methods further comprise determining the stability of the cross-linked protein. For example, the thermal and/or chemical stability can be determined as described herein and compared to the protein that has not been cross-linked. The biological activity of cross-linking can also be determined.

The present disclosure further provides cross-linkers having the formula (I):

(I)

wherein
Q is a core structure selected from the group consisting of

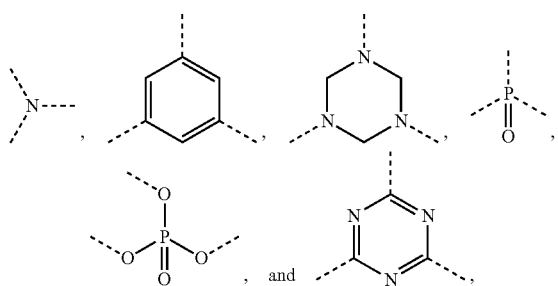

each dashed line in Q indicating a site where Q is bound to L,
each L is a linker independently selected from the group consisting of

wherein
each U is independently selected from $CH_2$ and $CF_2$,
V is $CH_2$
W is $CF_2$
X is NR, NH or O,
wherein R is a fluorophore or affinity handle,
n is an integer in the range of 2-8,
m is an integer in the range of 1-4
is 2 or 3, and
v is 2 or 3,
each dashed line in L indicating a site where L is bound to Q or E,
each E is an electrophile independently selected from the group consisting of

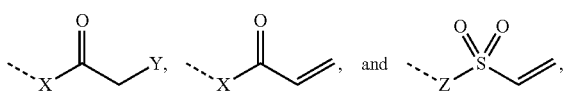

wherein
each X is independently selected from NH and O,
Y is selected from F, Cl, Br, Tos ($O-SO_2-C_6H_4-CH_3$), and Mes ($O-SO_2-CH_3$),
Z is $CH_2$, $NH-C(O)-CH_2$, or $O-C(O)-CH_2$
each dashed line in E indicating a site where E is bound to L.

Preferably, L is

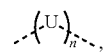

U is $CH_2$, preferably n is 2 or 3; and/or
E is

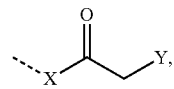

preferably wherein X is NH and Y is F, Cl, or Br, preferably Cl. While not wishing to be bound by theory, it is believed that trivalent cross-linkers having a non-hydrophic core (i.e, Q) are better suited to the cross-linking of proteins. In the known peptide stapling techniques which employ tris-electrophiles, cross-linkers with an aromatic core are generally used. In these cases, the core structures serve as the hydrophobic core to align non-polar amino acid side chains in its proximity. However, in the present preferred methods, a non-aromatic cross-linker will be located on the surface of the protein. Preferably, Q is

The present disclosure further provides cross-linkers having formula II:

(II)

wherein
Q is

each dashed line in Q indicating a site where Q is bound to L,
each L is a linker independently selected from the group consisting of

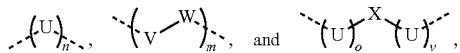

wherein
each U is independently selected from $CH_2$ and $CF_2$,
V is $CH_2$
W is $CF_2$
X is NR, NH or O,
wherein R is a fluorophore or affinity handle, n is an integer in the range of 2-8,
m is an integer in the range of 1-4
is 2 or 3, and
v is 2 or 3,
each dashed line in L indicating a site where L is bound to Q or E,
each E is an electrophile independently selected from the group consisting of

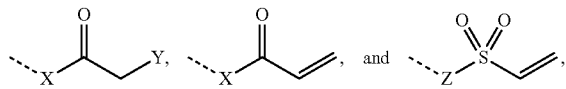

wherein
each X is independently selected from NH and O,
Y is selected from F, Cl, Br, Tos ($O-SO_2-C_6H_4-CH_3$), and Mes ($O-SO_2-CH_3$),
Z is $CH_2$, $NH-C(O)-CH_2$, or $O-C(O)-CH_2$
each dashed line in E indicating a site where E is bound to L.
Preferably, L is

U is $CH_2$, preferably n is 2 or 3; and/or
E is

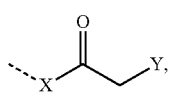

preferably wherein X is NH and Y is F, Cl, or Br, preferably Cl.
In a preferred embodiment, the cross-linker is Formula III:

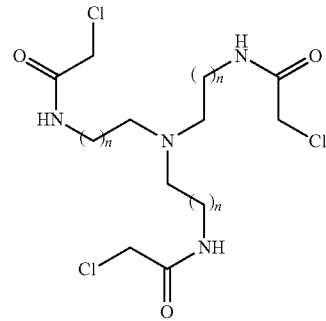

wherein n is 1 or n is 2. As demonstrated in the examples, such cross-linkers do not require organic solvents for solubility.

The cross-linkers described above are particularly useful for reacting with thiol groups. As such they can be used to cross-link cysteine residues and can be used as the trivalent thiol-reactive cross-linker, e.g., in the methods described herein.

The disclosure further provides a stabilized protein obtainable by a method as disclosed herein. In one embodiment, the disclosure provides a protein (as disclosed herein, e.g., comprising at least 70 amino acids and comprising at least three cysteine residues), wherein each of the three cysteine residues is covalently bonded to a trivalent thiol-reactive cross-linker. Preferably, the protein is cross-linked by a cross-linker having a formula of (I), (II), or (III). In an exemplary embodiment, the protein is a Sortase A (SrtA) polypeptide. Preferably, the SrtA is cross-linked with formula (III).

SrtA is a transpeptidase belonging to the Sortase family of prokaryotic enzymes. It is an important biomolecular tool allowing specific labeling of proteins.[16-18] However, when higher temperatures or denaturants are required, labeling efficiency drops dramatically limiting the applicability of this enzyme. As described in the examples, the disclosure describes the generation of a SrtA polypeptide having a cysteine at positions 111, 149, and 177, with reference to amino acid position numbering of *Staphylococcus aureus* SrtA. Cross-linking this modified protein with a trivalent thiol-reactive cross-linker resulted in a 11.2° C. increase in melting temperature and an increased resistance to guanidinium hydrochloride, indicating an increase in stability. In a preferred embodiment, the SrtA polypeptide has the amino acid sequence:

(SEQ ID NO: 1)
GSHMQAKPQIPKDKSKVAGYIEIPDADIKEPVYPGPATPEQLNRGVSFA

EENESLDDQNISIAGHTFIDRPNYQFTNLKAAKKGSMVYFKVGNETRKY

KMTSIRDVKPTDVGVLDEQKGKDKQLTLITCDDYNEKTGVWEKRKIFVA

TEV.

As described in the examples, cross-linked SrtA, as disclosed herein, can be used in protein labeling experiments under conditions where the wildtype (non-crosslinked) SrtA does not provide sufficient activity. The disclosure further provides the use of the cross-linked SrtA, as disclosed herein for protein/cell labeling, preferably in the presence of a chemical denaturing agent such as guanidinium hydrochloride.

In an exemplary embodiment, the protein is a KIX domain polypeptide. Preferably, the KIX domain is cross-linked with formula (III) or formula (IV). The disclosure provides KIX domain polypeptides comprising three cysteine residues is covalently bonded to a trivalent thiol-reactive cross-linker.

As used herein, "to comprise" and its conjugations is used in its non-limiting sense to mean that items following the word are included, but items not specifically mentioned are not excluded. In addition the verb "to consist" may be replaced by "to consist essentially of" meaning that a compound or adjunct compound as defined herein may comprise additional component(s) than the ones specifically identified, said additional component(s) not altering the unique characteristic of the invention.

The articles "a" and "an" are used herein to refer to one or to more than one (i.e., to at least one) of the grammatical object of the article. By way of example, "an element" means one element or more than one element.

The word "approximately" or "about" when used in association with a numerical value (approximately 10, about 10) preferably means that the value may be the given value of 10 more or less 1% of the value.

The invention is further explained in the following examples. These examples do not limit the scope of the invention, but merely serve to clarify the invention.

EXAMPLES

Example 1

Here we report a structure-based strategy for the stabilization of enzymes via post-translational modification of proteins entirely composed of proteinogenic amino acids. A library of biselectrophiles was used to staple a set of enzyme variants presenting pairs of accessible cysteine residues (FIG. 1a). Based on the stabilization behavior of the resulting monocyclic proteins, a bicyclic enzyme was designed that shows greatly increased tolerance towards thermal and chemical denaturation.

Figure 1B:
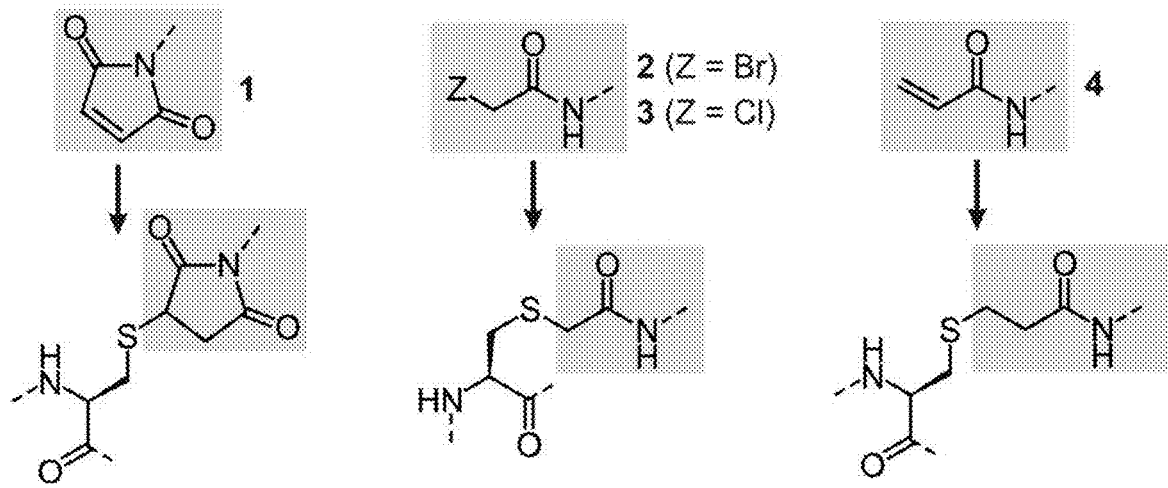
Figure 2A:
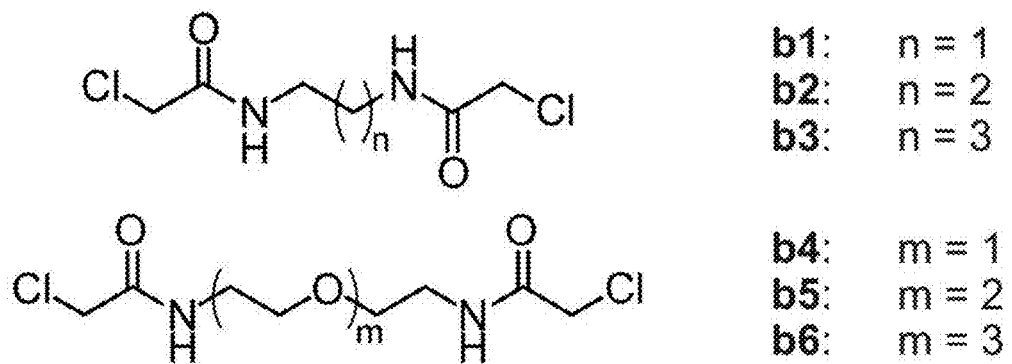
FIG. 2. a) Biselectrophiles (b1-b6) used for the generation of cyclic enzymes; b) NMR structure of SrtA (PDB: 1ija) with positions of cysteine variations high-lighted. Cysteine pairs (same color) and their positions are shown; c) Heat map representation of Tm-values for linear and crosslinked SrtA variants (75 µM); d) Mechanism for SrtA-mediated transpeptidation reactions (recognition motif: LPETG, SEQ ID NO: 9); e) Heat map representation of enzymatic activity (vr, relative to wildtype SrtA) of linear and crosslinked SrtA variants at 65° C. (10 µM enzyme, 10 µM fluorescent probe) (buffer for 2c and 2e: 20 mM HEPES, pH 7.5, 150 mM NaCl, 5 mM CaCl2), 2 mM TCEP with 0.01% TWEEN for 3e).
Figure 5:
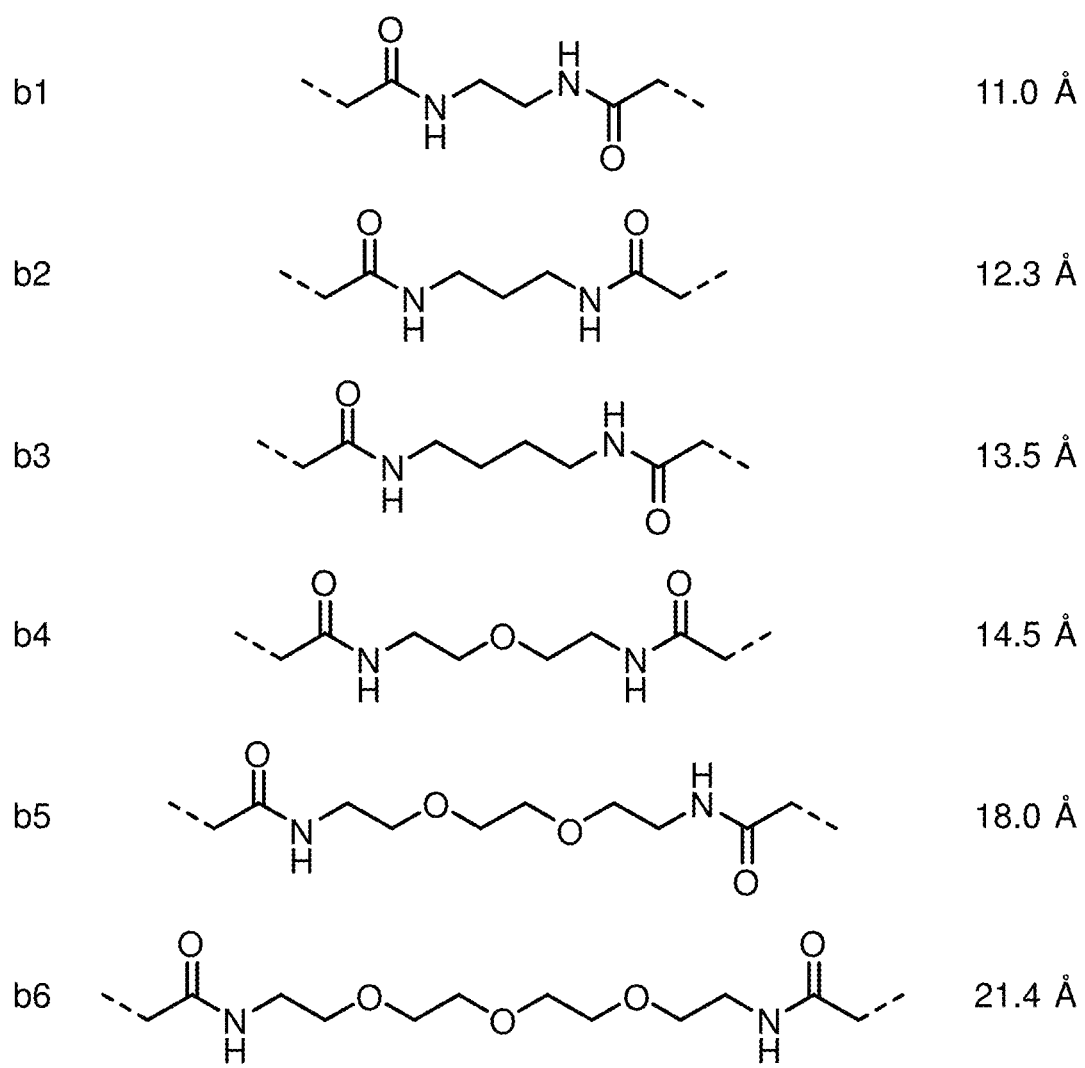
FIG. 5: Chemical structure of biselectrophilic cross-linkers and their calculated lengths using 3D ChemDraw.

We chose *Staphylococcus aureus* Sortase A (SrtA, aa 60-206) as the target for our stabilization efforts. To stabilize SrtA, we considered a crosslinking strategy that has previously been applied to constrain peptides[19-23] and involves the use of biselectrophiles that target pairs of cysteine residues. SrtA contains a single cysteine located in the active site which is crucial for its activity. Initially, we tested four electrophiles (1-4, FIG. 1b) that have previously been used for the covalent modification of solvent exposed cysteines to seek for a functionality that does not react with the active site cysteine. Conditions suitable for preparative scale protein modification led to substantial modification of this crucial cysteine when incubated with the two most reative electrophiles maleimide (1) and 2-bromo¬acetamide (2) but not for 2-chloro¬acetamide (3) and acrylamide (4). As thiols tend to show reversible addition to acrylamides, we chose 2-chloroacetamide as the electrophile and designed a set of biselectrophilic linkers with 8-17 bridging atoms (b1-b6, FIG. 2a) spawning a broad range of distances (up to 21 Å, FIG. 5).

Figure 2B:
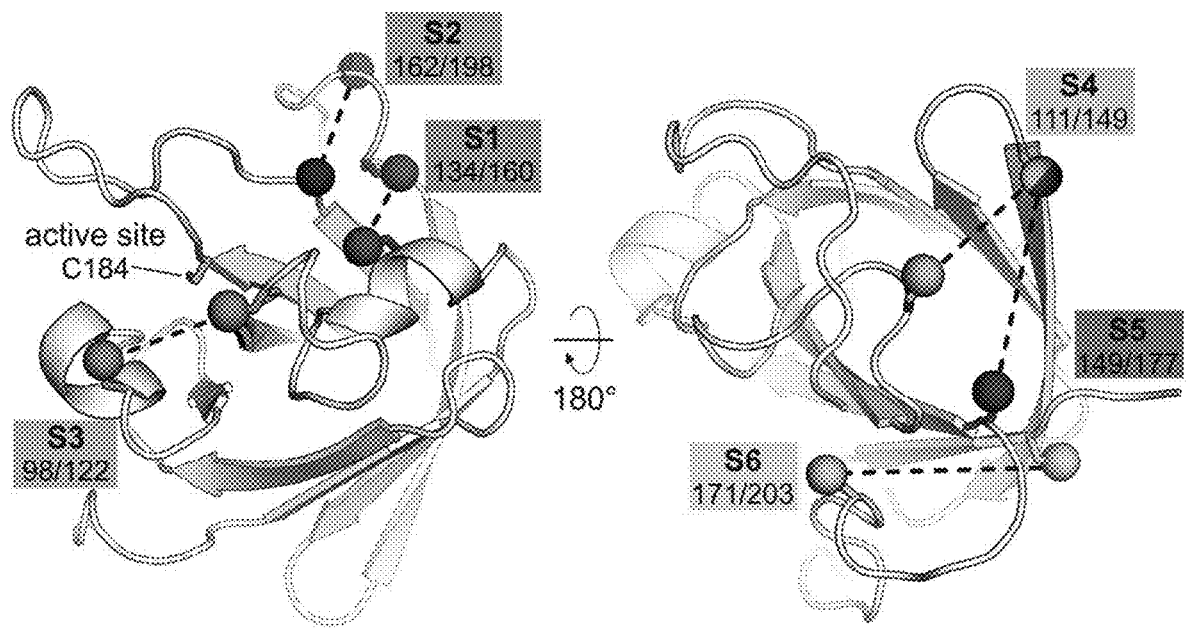

Next, suitable positions for the introduction of cysteine pairs in SrtA were selected aiming for a stabilization of the overall tertiary structure. We considered (i) surface residues not involved in substrate recognition and selected pairs (ii) that are located in two different secondary structure elements (iii) while still being in spacial proximity (distance <20 Å, based on NMR structure, PDB: 1ija). Based on these criteria, six SrtA variants (S1-S6, FIG. 2b, FIG. 6) were designed, heterologously expressed in *E. coli* and purified. Subsequently, stapling reactions with all bis-electrophiles were performed showing various degrees of conversion. Formation of the cyclization product was confirmed by MS and SDS-PAGE. While we observed high conversions for S1, S3, S4 and S6 with all crosslinks, S5 showed low efficiency with the shortest crosslink (b1). For S2, low yields were observed for all cross-linkers. After the reaction, protein samples were dialyzed to remove unreacted biselectrophiles.

Figure 2C:
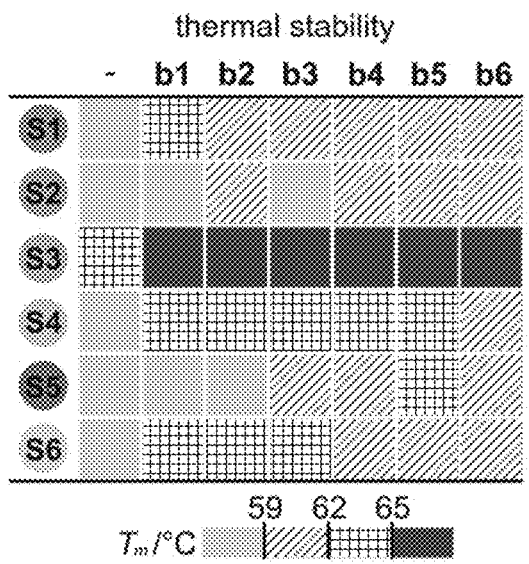

Initially, the melting temperatures (Tm) of all unmodified and crosslinked variants (as obtained after dialysis) were determined via changes in tryptophan fluorescence (FIG. 2c). Compared to SrtA (Tm=59.4° C.), all non crosslinked variants show a lower thermal stability except for S3 (ΔTm=+2.9° C.). Enzyme cross-linking results in strong stabilization of the cyclic S3 versions (ΔTm≥+10.1° C.) while more moderate effects were observed for the remaining variants. The most stable versions per variant are S1 b1 (ΔTm=+2.8° C.), S2 b2 (ΔTm=+0.4° C.), S4 b3 (ΔTm=+4.4° C.), S5 b5 (ΔTm=+3.4° C.) and S6 b1 (ΔTm=+3.9° C.).

Figure 7B:
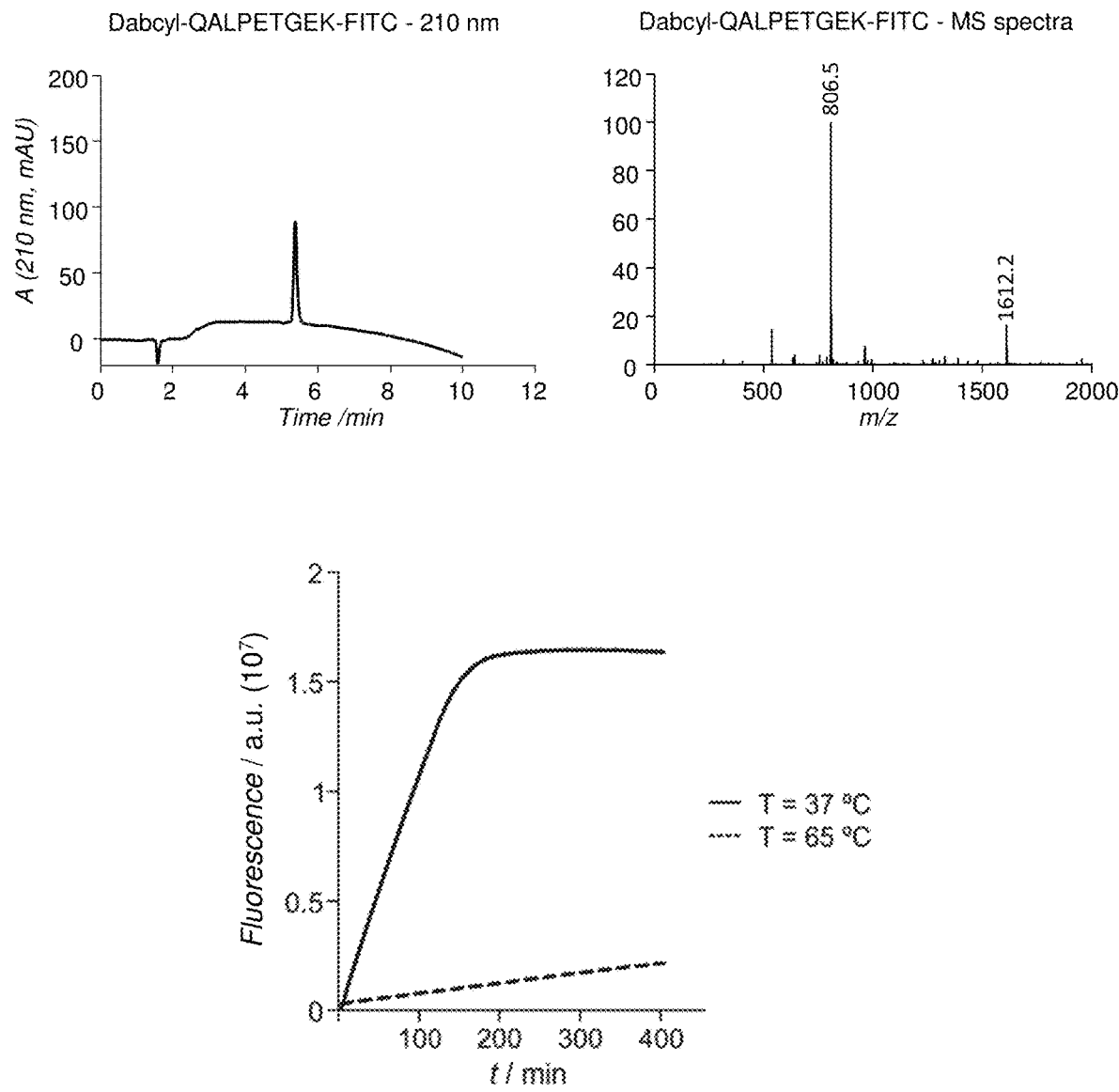
FIG. 7: a) Schematic depiction of SrtA enzymatic activity assay. Chemical structure, HPLC chromatogram (linear gradient from 30% to 70% ACN over 10 min, 210 nm) and MS spectra of fluorescence probe. b) Plot of SrtA hydrolysis activity assay at 37° C. (solid line) and 65° C. (dashed line).

SrtA is a transpeptidase that recognizes a short peptide sequence (LPETG, SEQ ID NO: 9, FIG. 2d), cleaves it and forms an acyl intermediate with its N-terminal fragment. The intermediate is then attacked preferably by the N-terminus of an oligo-glycine (FIG. 2d) to form a new peptide bond. In absence of a suitable nucleophile, water will attack and hydrolyze the acyl intermediate (FIG. 2d). To investigate transpeptidase activity, a previously reported probe system was applied in which a fluorophore/quencher pair is separated upon SrtA processing (FIG. 7). For activity screening, we chose the hydrolysis reaction[24,25] at 65° C., where wildtype SrtA shows strongly reduced performance (4% residual activity, FIG. 7). Relative to SrtA (vr=1, FIG. 2e), a number of crosslinked enzymes show increased activity.

Figure 2E:
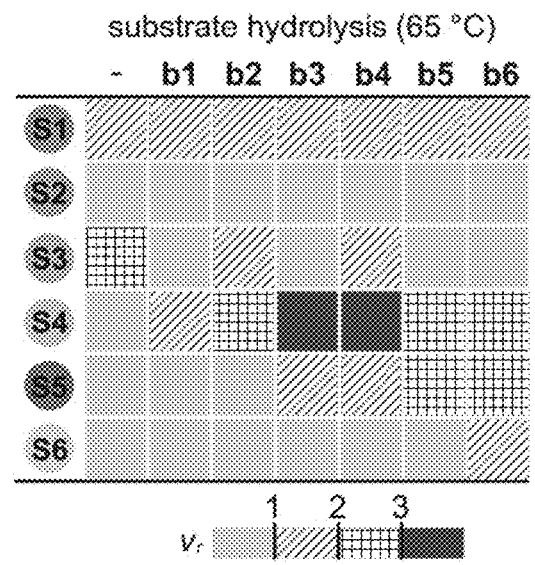
Figure 2D:
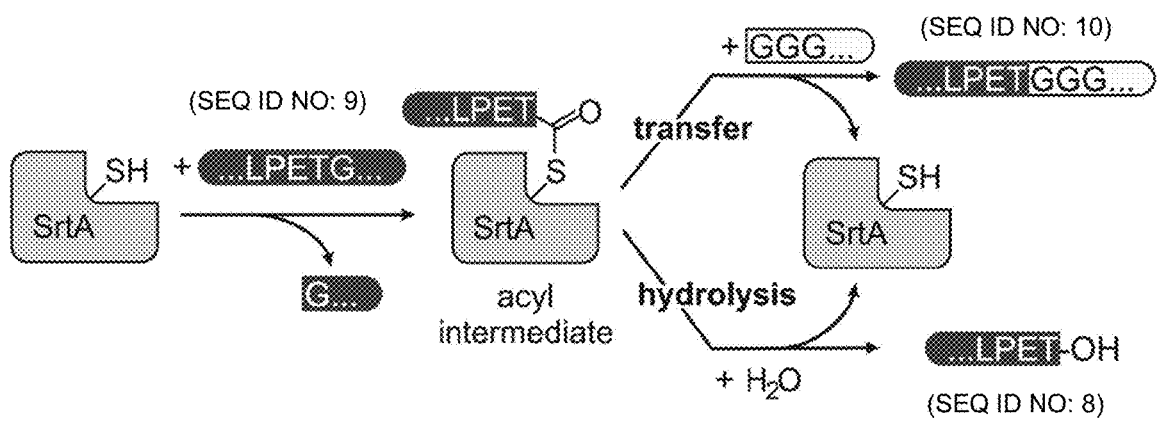

Surprisingly, the thermostable cyclic versions of S3 provide reduced enzymatic activity (FIG. 2e). In contrast, crosslinked versions of S4 and S5 show robust activity enhancements (>2-fold, light and dark red, FIG. 2e). The overall highest increase in activity was observed for S4-b3, which is 3.4 fold more active than SrtA. Taken together, observed improvements in activity at 65° C. are moderate indicating that mono-cyclization may not be sufficient to convey enough stabilization of the tertiary structure.

Figure 3A:
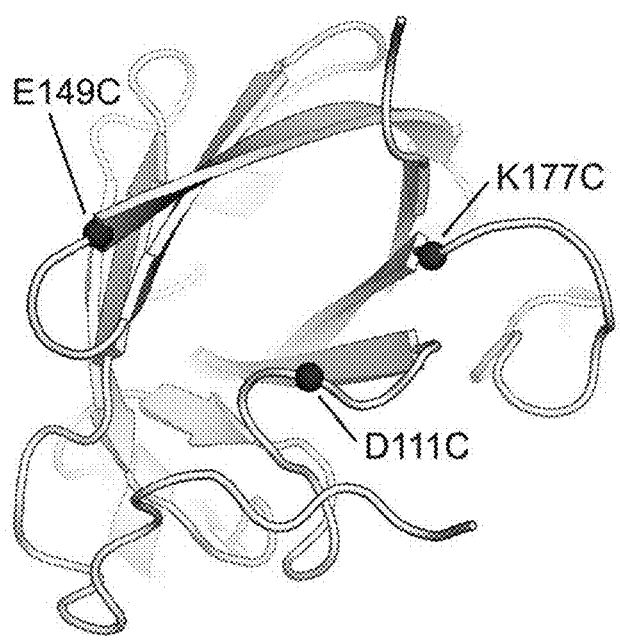
FIG. 3. a) NMR structure of SrtA (PDB: 1ija) with positions of cysteine variations in S7 highlighted; b) Chemical structure of triselectrophile t1 and Coomassie-stained SDS-PAGE gel showing protein bands after incubation t1 (50 μM S7, 1 mM t1, 50 mM HEPES, pH 8.5, 150 mM NaCl, 5 mM CaCl2), 2 mM TCEP); c) Melting curves of SrtA, S4-b3 and S7-t1 including Tm-values; d) Fluorescent readout of probe cleavage upon enzyme activity at 65° C. (10 μM enzyme, 10 μM fluorescent probe) (buffer for 3c and 3d: 20 mM HEPES, pH 7.5, 150 mM NaCl, 5 mM CaCl2), 2 mM TCEP with 0.01% TWEEN for d).
Figure 3B:
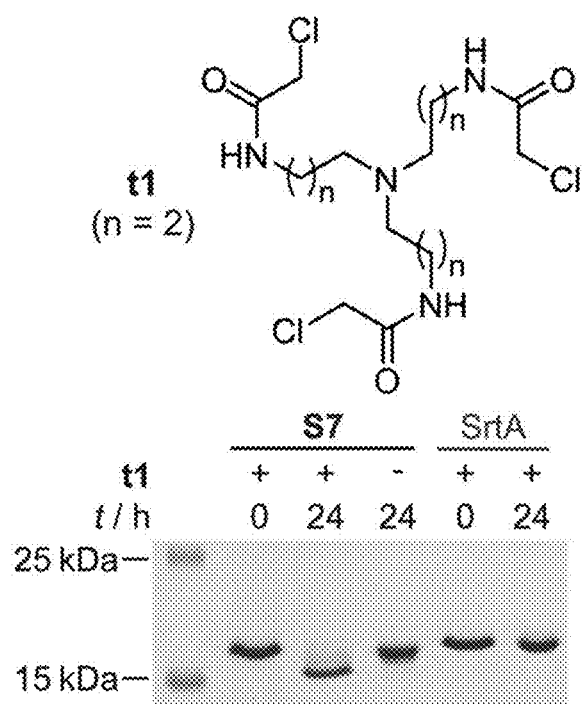

To achieve a stronger stabilization of the protein tertiary structure, we aimed for a bicyclization of the enzyme. Notably, the two best performing SrtA variants S4 and S5 (light and dark blue, FIG. 2b) share one variation site (aa 149). The simultaneous introduction of their cysteine substitutions (aa 111, 149 and 177) generates variant S7 (FIG. 3a), which can form a bicyclic protein upon reaction with a triselectrophile. In analogy to the previously reported synthesis of bicyclic peptides[26-28] and mini-proteins[29], we selected a C3 symmetric core for our cross-linker, which we modified with three 2-chloroacetamide groups (t1, FIG. 3b). Triselectrophile t1 was designed to provide 13 bridging atoms thereby lying between the preferred crosslink ranges for S4 (b3/b4: 10/11 atoms) and S5 (b5/b6: 14/17 atoms). The crosslinking reaction of S7 and t1 proceeds efficiently and provides the stapled enzyme S7-t1 (FIG. 3b).

Figure 8B:
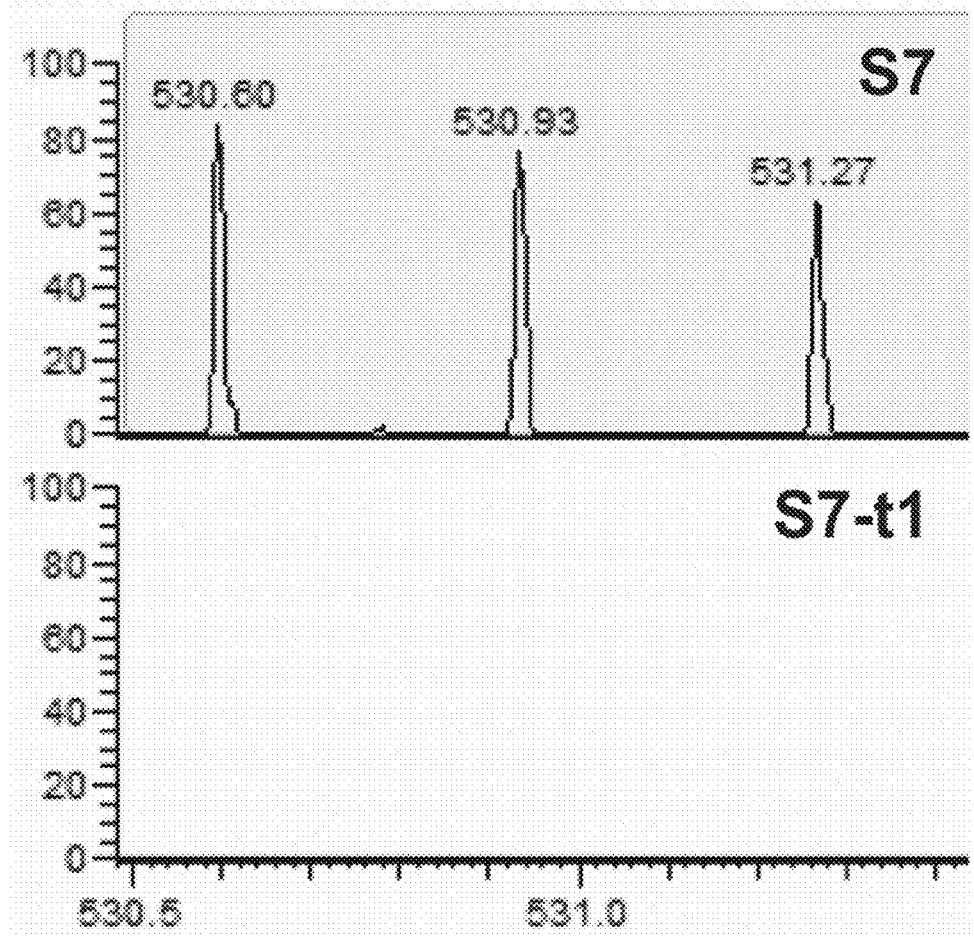
FIG. 8: Analysis of the modification state of the four cysteines in S7 and S7-t1 by HPLC-coupled high-resolution mass spectrometry. The spectra for the following tryptic fragments are shown:
  a) aa 100-134 (including C111), b) 138-151 (including C149), c) 176-190 (including C177 and active site C184). Free cysteine residues or C4H4ON (grey) modified ones indicate a free cysteine in the enzyme (S7 or S7-t1) before MS workup, while C2H2O (red) modified cysteines indicate a covalent modification with t1.

Analytical HPLC/MS analysis indicates quantitative conversion of S7, clearly showing the formation of a product with the expected molecular weight. High-resolution MS analysis confirms the correct modification sites (cysteines 111, 149 and 177) also verifying the unmodified state of the active site cysteine after stapling (FIG. 8).

Investigating the thermal stability of S7-t1, we observed a greatly increased melting temperature (Tm=70.6° C., FIG. 3c). This is 11.2° C. higher than the value of SrtA (Tm=59.4° C.) and 6.8° C. higher than that of the most active mono-cyclic protein S4-b3 (Tm=63.8° C.). Next, we determined the enzymatic activity of S7-t1 at 65° C. (FIG. 3d) as described for the mono-cyclic versions. In line with its superior thermal stability, we observe a strongly increased enzymatic activity at 65° C. when compared to SrtA (8.7-fold) and to the most active mono-cyclic enzyme S4-b3 (2.6-fold, FIG. 3d).

Figure 11:
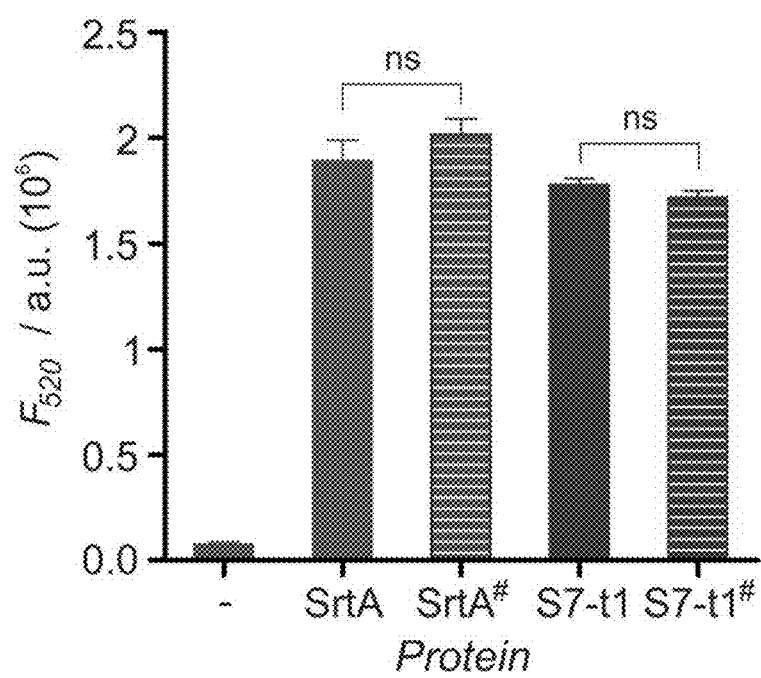
FIG. 11: Transpeptidase activity of StrA (grey) and bicyclic S7-t1 (red) before and after thermal denaturation. Untreated proteins (StrA and S7-t1) and samples subjected to a heating/cooling cycle (StrA # and S7-t1 #, heating from r.t. to 85° C. over 30 min and cooled to r.t. over 15 min) are compared. A sample without enzyme was included (−). Statistical significance was evaluated by an unpaired t test (n=3, ns: not significant p >0.05).

So far, we investigated enzyme activity under hydrolytic conditions using water as the nucleophile (hydrolysis, FIG. 2d). Envisioning the application of S7-t1 for protein labeling, we next investigated its transpeptidation performance at 65° C. with the above described fluorescent probe but now in the presence of the nucleophile triglycine (transfer, FIG. 2d). Using HPLC/MS as a readout (FIG. 4a), we again observed only very weak substrate conversion with SrtA (dark grey) similar to a treatment without any enzyme (light grey). In the presence of S7-t1 (red, FIG. 4a), the signal of the starting material (●), was greatly diminished and two new peaks appeared. Based on the MS, one peak was assigned to the C- (▲) and the other one to the N-terminal fragment (■), which appears to be ligated to triglycine. Importantly, a signal for the hydrolysis product (Dabcyl-QALPET, SEQ ID NO: 3) was not detected verifying the correct functionality of S7-t1. To assess if protein unfolding under elevated temperature is reversible, we compared the enzymatic activity of SrtA and S7-t1 at 37° C. before and after heating (85° C. FIG. 11). Notably, the transpeptidase activity of both enzymes is not affected by the heating/cooling cycle indicating reversible unfolding.

In a next set of experiments, we determined the thermal activity profile of the transpeptidation reaction using again the fluorescent readout (FIG. 4b). Between 37° C. and 55° C., the enzymatic activity of SrtA (grey) and S7-t1 (red) is similar exhibiting only weak temperature dependence. Above 55° C., both enzymes experience a loss in activity which is very severe for SrtA resulting in almost complete inactivation at 65° C. (FIG. 4b). For S7-t1, the activity reduction is much smaller with a residual activity of 63% (at 65° C.) and 27% (at 70° C.) relative to 37° C. Compared to SrtA, S7-t1 shows a ~10° C. increased tolerance towards thermal stress which correlates well with its +11.2° C. higher melting temperature. Enhanced thermal stability often goes in hand with a resistance towards denaturants such as guanidinium hydrochloride (GdnHCl). For that reason, the impact of GdnHCl on the transpeptidase activity was investigated (FIG. 4c), revealing low dependence of SrtA and S7 t1 on the denaturant concentration up to 0.5 M. Between 0.75 and 1.5 M, S7-t1 is significantly more active than SrtA. Most notably at 1 M GdnHCl, SrtA does not show any detectable enzyme activity (vr <1%, FIG. 4c) while S7-t1 still provides 40% residual activity (compared to absence of GdnHCl). At higher GdnHCl concentrations (≥2 M) both enzymes lose their enzymatic activity.

Figure 9B:
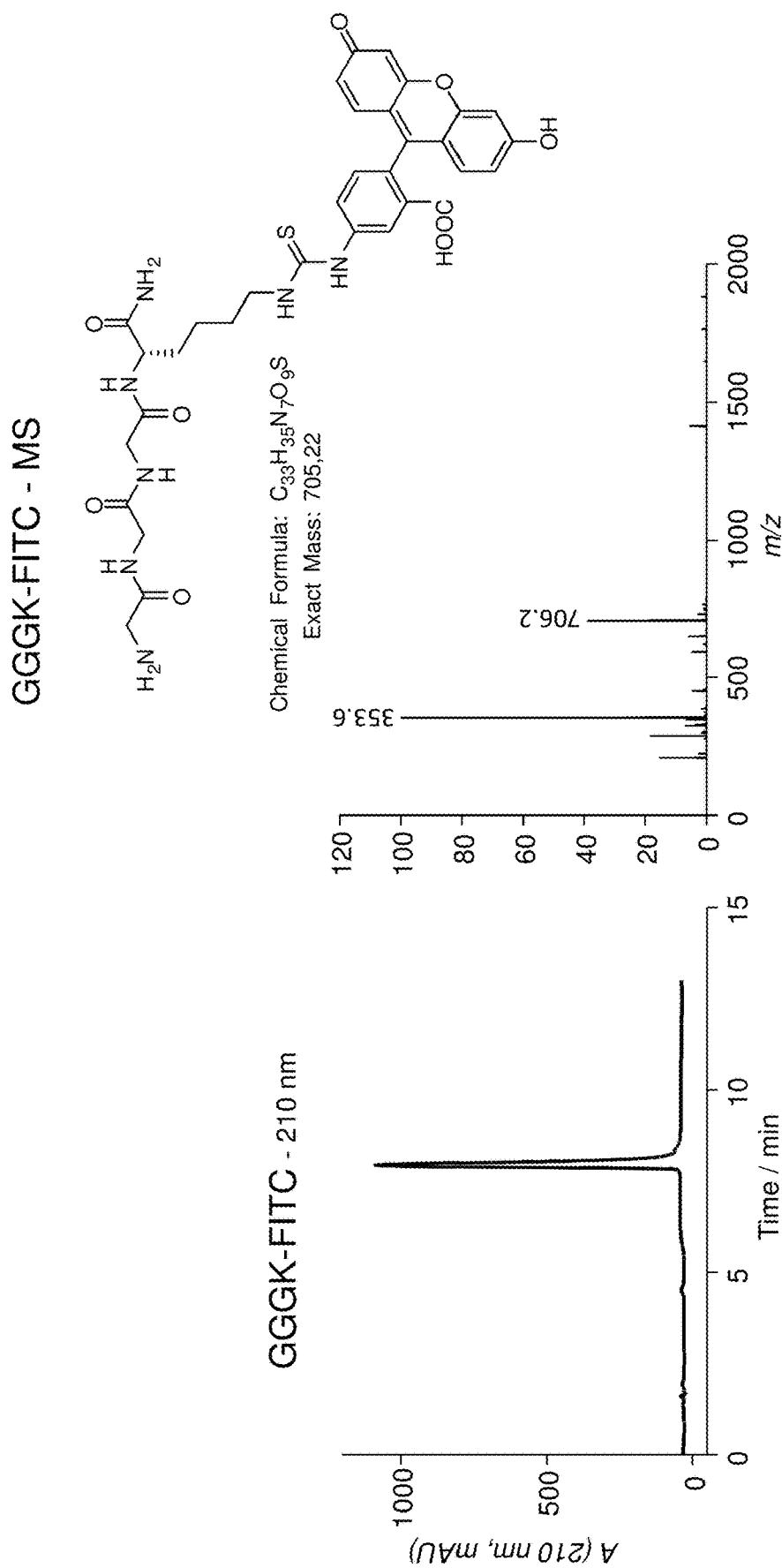
FIG. 9: a) SEQ ID NO:2: α-Synuclein (α-Syn) sequence including a C-terminal flexible linker (bold), SrtA recognition motif (grey) and a His6-tag (underlined) for affinity purification. b) Chemical structure and HPLC/MS analysis of the fluorescent probe GGGK-FITC. Chromatogram ($\lambda$=210 nm) and MS spectrum are shown.

So far, we have applied S7-t1 for the labeling of a short test peptide. Next, we were interested if S7-t1 is also useful for protein labeling in particular under conditions where wildtype SrtA does not provide sufficient activity. For that purpose, we chose α-Synuclein (α-Syn) as the protein of interest. α-Syn comprises 140 amino acids and can form pathogenic fibrils which are associated with the onset of various neurodegenerative diseases including Parkinson's.[30] α Syn fibrils can be solubilized using GdnHCl.[31] We designed an α Syn version with a C-terminal SrtA-recognition motif to allow labeling. Following expression and purification, soluble α-Syn (A) was subjected to fibril formation and ultra-centrifugation.[31] Insoluble fibrils were washed and treated with buffer either lacking (B) or containing (C) GdnHCl (1 M).[31] When comparing the resulting soluble fractions (B and C) with the purified and soluble form of α-Syn (A, FIG. 4d), we clearly observed re-solubilization only in the presence (C) but not in absence (B) of GdnHCl. To investigate protein labeling, these soluble samples (A, B, C) were incubated with either SrtA or S7-t1, and a fluorescent substrate (FIG. 9). We then performed analysis via SDS-PAGE employing a fluorescence imager for the readout. For soluble α-Syn prior fibril formation (A) and therefore in absence of GdnHCl, SrtA and S7-t1 result in intense bands indicating efficient protein labeling (FIG. 4e). As expected, under re-solubilization conditions lacking GdnHCl (B) and therefore also lacking soluble α-Syn, we did not observe any fluorescent signal (B, FIG. 4e). On the contrary, for re-solubilization with GdnHCl (1 M), α-Syn labeling occurs but only with S7-t1 and not with wildtype SrtA (C). Notably, differences in the fluorescent band intensities for S7-t1 (A vs. C, FIG. 4e) correlate well with the amount of α-Syn in the soluble fractions (A vs. C, FIG. 4d) indicating good labeling efficiencies for S7 t1 in the presence of GdnHCl.

Figure 12A:
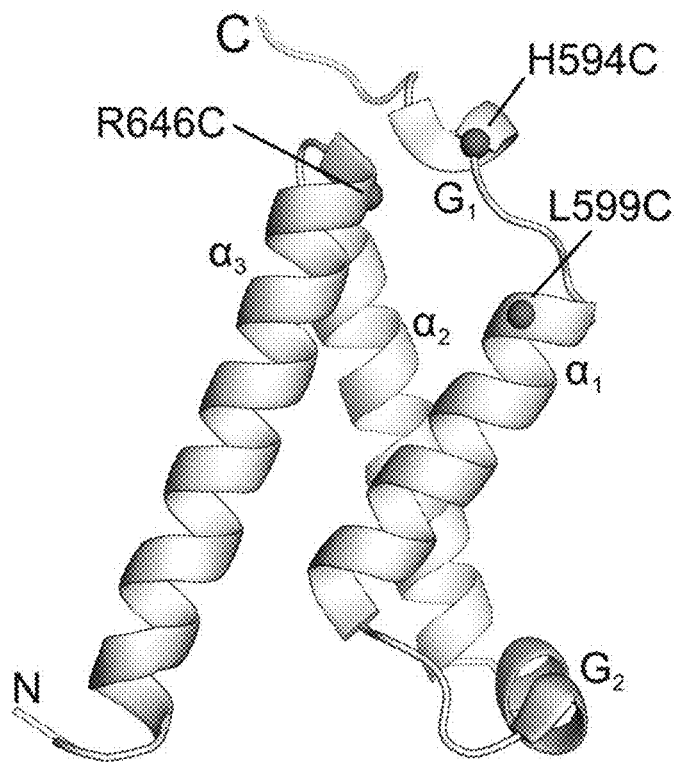
FIG. 12. a) NMR structure of KIX (PDB: 2agh) with positions of cysteine variations in K1 highlighted. The secondary structural elements have been named; b) Melting curves of KIX, K1-t1 and K1-t2 including Tm-values.
Figure 12B:
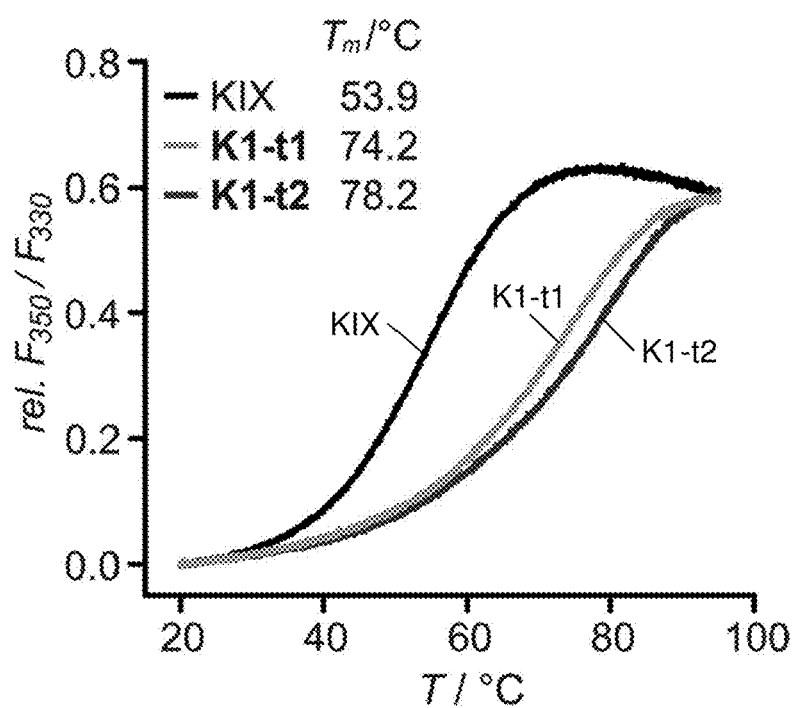

To assess the broader applicability of protein stabilization via bicyclization, we chose the KIX domain from the human CREB binding protein as a second target (FIG. 5a). KIX is an adaptor domain with multiple protein binding partners that is composed of a central three α helix bundle (α1, α2, α3). The junction between this bundle and the C-terminal 310 helix (G1) is crucial for structural integrity (FIG. 12a).[34] Thus, we focused on this area for tertiary structure stabilization searching for three positions suitable for cysteine incorporation. Based on our experiences during SrtA stabilization, the following guidelines were applied: (i) Solvent accessible residues were considered, that are (ii) located in three distinct secondary structures, while (iii) facing the same side of the protein and (iv) spanning a triangle with side lengths between 6 and 17 Å (Cα-Cα distance). Based on these criteria, we selected H594, L599 and R646 for cysteine substitution resulting in KIX variant K1 (FIG. 12a, FIG. 12).

Figure 14A:
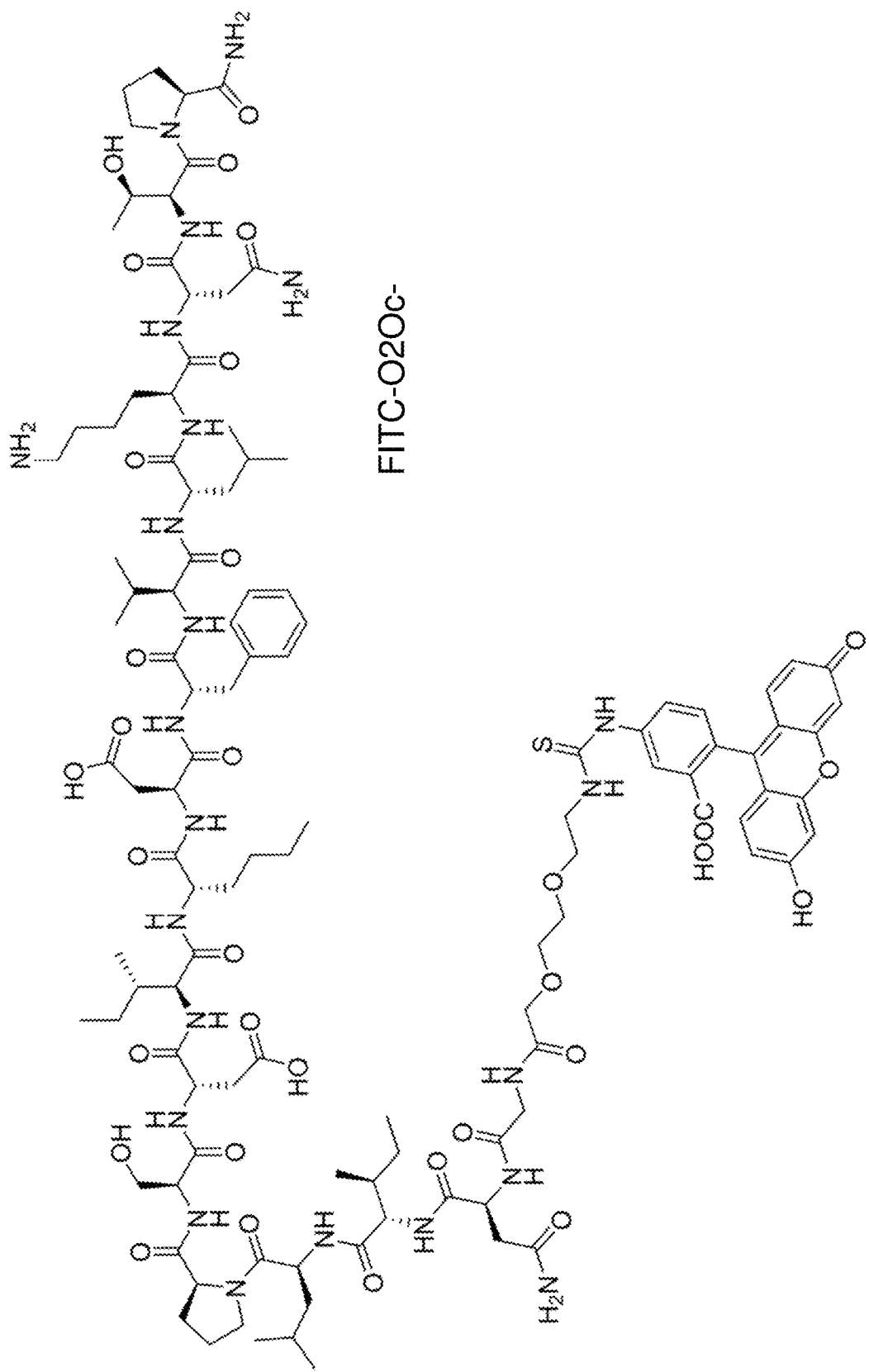
FIG. 14: a) Chemical structure, HPLC chromatogram (linear gradient from 40% to 80% ACN over 10 min (3-13 min), $\lambda$=210 nm) and MS spectra of MLL peptide. b) FP assay of KIX wt and crosslinked versions K1-t1 and K1-t2. The corresponding Kd values are shown.
Figure 14B:
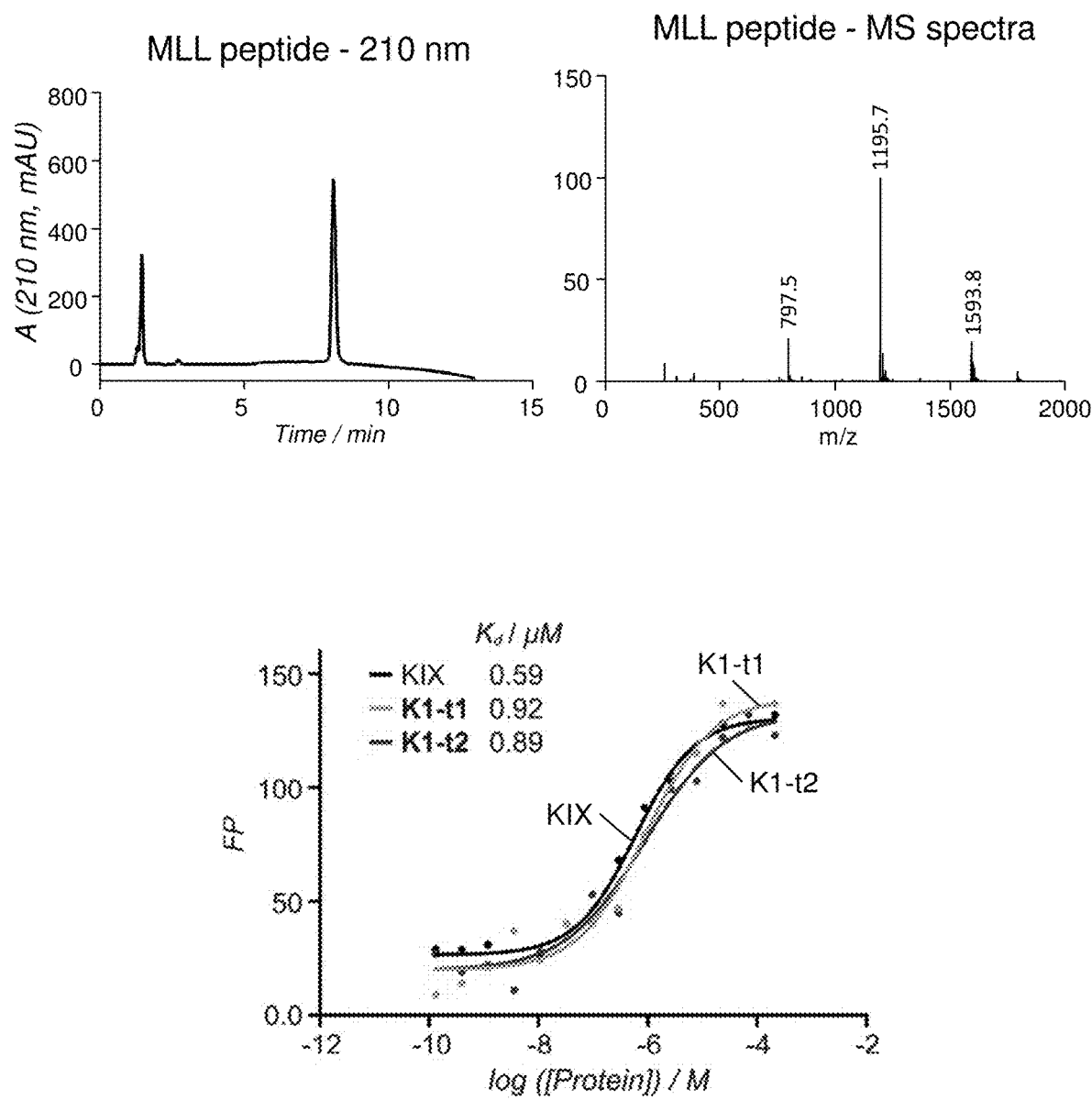
Figures 15A, 15B:
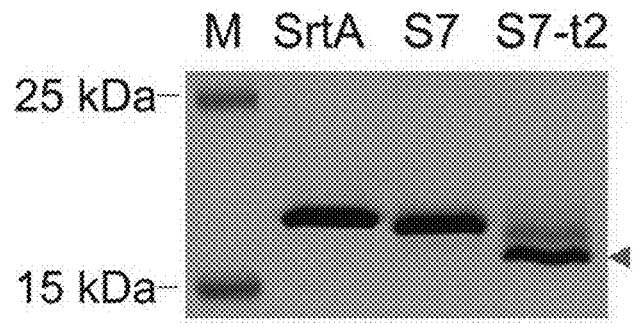
FIG. 15: a) Coomassie-stained SDS-PAGE gel showing protein bands after incubation with t2 (50 μM S7, 1 mM t2, 50 mM HEPES, pH 8.5, 150 mM NaCl, 5 mM CaCl2), 2 mM TCEP). b) Table with calculated and found m/z-values for S7-t2. c) MS spectra of bicyclic S7-t2. d) Melting curves of SrtA and S7-t2 including apparent Tm-values. e) Fluorescent readout of probe cleavage upon enzyme hydrolytic activity at 65° C. (10 μM enzyme, 10 μM fluorescent probe). Buffer used for experiments d and e: 20 mM HEPES, pH 7.5, 150 mM NaCl, 5 mM CaCl2), 2 mM TCEP, with 0.01% TWEEN 20 for e).
Figure 15C:
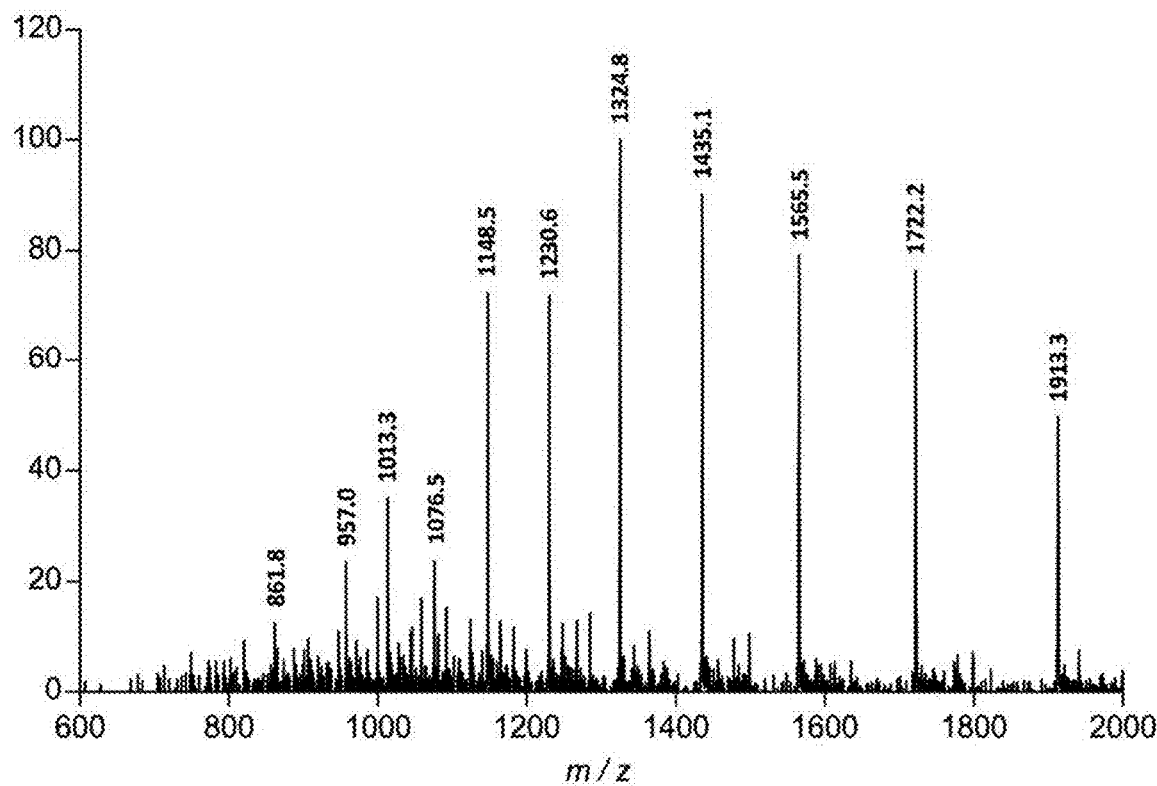
Figure 15D:
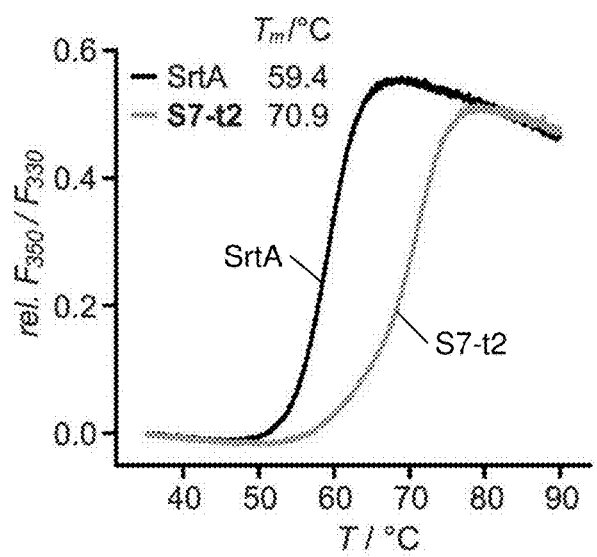
Figure 15E:
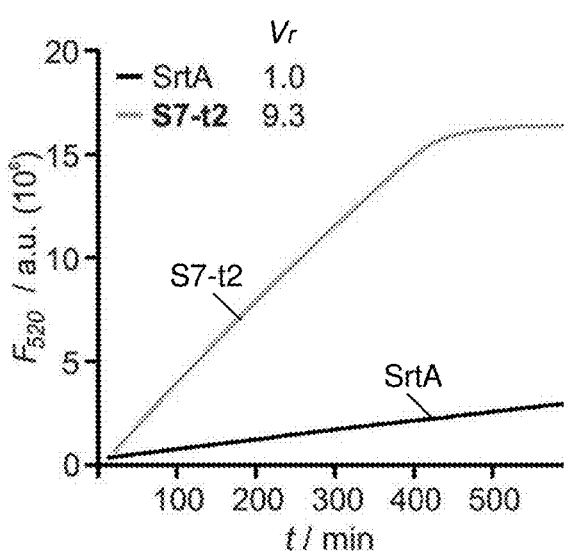

For crosslinking, we chose triselectrophile t1 (n=2, FIG. 3b) and a shorter version t2 (n=1) since we noticed that the distances between the three variation sites in K1 (7.8, 10.0 and 11.5 Å, FIG. 12) are shorter than in S7 (8.5, 12.4 and 15.7 Å, FIG. 13d). The crosslinking with both triselectrophiles proceeds efficiently as confirmed by SDS-PAGE and HPLC-MS analysis (data not shown). To evaluate if crosslinking affects the tertiary structure, we compared the affinity of KIX and both bicyclic variants (K1-t1 and K1-t2) to its binding partner MLL. Using a fluorescence polarization assay, we observed similar binding affinities for KIX, K1-t1 and K1-t2 (Kd=0.6, 0.9 and 0.9 μM, respectively, FIG. 14). Then, we measured apparent melting temperatures for the three proteins (FIG. 12b) to find a strongly increased thermal stability for K1-t1 and K1-t2 (ΔTm=+20.6° C. and +24.6° C., respectively) when compared to KIX. Notably, both triselectrophiles have a similar stabilizing effect with the shorter crosslink t2 performing best. Based on these results, we were also interested to evaluate the effect of triselectrophile t2 on StrA variant S7. The crosslinking reaction proceeds efficiently resulting in bicyclic enzyme S7-t2 (FIG. 15). Notably, we observe a similar thermal stabilization for S7-t2 (ΔTm=+11.5° C., FIG. 15) as for S7-t1 (ΔTm=+11.2° C.), indicating tolerance towards minor variabilities in the length of the crosslink.

In summary, we report a structure-based approach for the stabilization of enzymes that allows the installation of modular crosslinks into native proteins composed entirely of proteinogenic amino acids. We explored a series of monocyclized SrtA variants leading to the design of the bicyclic enzyme S7 t1 which exhibits greatly increased tolerance towards thermal and chemical denaturation. Importantly, S7 t1 proved efficient in labeling α-Syn in presence of 1 M GdnHCl. Under these conditions, wildtype SrtA did not show enzymatic activity. Even though, we did not encounter this problem with our SrtA variants, it is important to note that additional surface exposed cysteine residues can lead to undesired side products during the cyclization reaction. In such cases, it would be necessary to vary these cysteines (e.g. to serine) or if required for catalytic activity to block the active site during crosslinking. From our findings with SrtA, we derived guidelines for the bicyclization and stabilization of a protein and applied them to the KIX domain. A three cysteine KIX variant was designed and reacted with two different C3-symmentric triselectrophiles resulting in two bicyclic KIX versions both with greatly increased thermal stability. Overall, our approach facilitates a structure-based stabilization of recombinant proteins which are entirely composed of proteinogenic amino acids. The use of synthetic electrophiles for protein cyclization gives straightforward access to diverse and tunable crosslink architectures. As an additional feature, we envision the use of crosslinking agents that allow the introduction of an additional functionality such as an affinity handle (e.g. for enzyme purification/recycling)[32] or a ligand for proximity-based sortase-mediated ligation.[33] Taken together, the presented protein stabilization technology holds the potential to give rapid access to novel stabilized enzymes providing the opportunity for a simultaneous incorporation of additional functions.

REFERENCES

[1] U. T. Bornscheuer, G. W. Huisman, R. J. Kazlauskas, S. Lutz, J. C. Moore, K. Robins, Nature 2012, 485, 185-194.
[2] C. P. R. Hackenberger, D. Schwarzer, Angew. Chem. Int. Ed. 2008, 47, 10030-10074.
[3] A. J. Keefe, S. Jiang, Nat. Chem. 2012, 4, 59-63.
[4] J. Milton Harris, R. B. Chess, Nat. Rev. Drug Discov. 2003, 2, 214-221.
[5] M. T. Reetz, Angew. Chem. Int. Ed. 2013, 52, 2658-2666.
[6] C. Jost, A. Plückthun, Curr. Opin. Struct. Biol. 2014, 27, 102-112.
[7] T. J. Magliery, Curr. Opin. Struct. Biol. 2015, 33, 161-168.
[8] A. M. Chapman, B. R. McNaughton, Cell Chem. Biol. 2016, 23, 543-553.
[9] F. Agostini, J. S. Valler, B. Koksch, C. G. Acevedo-Rocha, V. Kubyshkin, N. Budisa, Angew. Chem. Int. Ed. 2017, 56, 9680-9703.
[10] N. Martínez-Sáez, S. Sun, D. Oldrini, P. Sormanni, O. Boutureira, F. Carboni, I. Compañón, M. J. Deery, M. Vendruscolo, F. Corzana, et al., Angew. Chem. Int. Ed. 2017, 56, 14963-14967.
[11] J. A. Camarero, T. W. Muir, J. Am. Chem. Soc. 1999, 121, 5597-5598.
[12] H. Iwai, A. Plu, FEBS Lett. 1999, 459, 166-172.
[13] C. Schoene, J. O. Fierer, S. P. Bennett, M. Howarth, Angew. Chem. Int. Ed. 2014, 53, 6101-6104.
[14] E. J. Moore, D. Zorine, W. A. Hansen, S. D. Khare, R. Fasan, Proc. Natl. Acad. Sci. 2017, 201708907.
[15] J. W. Chin, EMBO J. 2011, 30, 2312-2324.
[16] C. P. Guimaraes, M. D. Witte, C. S. Theile, G. Bozkurt, L. Kundrat, A. E. M. Blom, H. L. Ploegh, Nat. Protoc. 2013, 8, 1787-1799.
[17] J. J. Bellucci, J. Bhattacharyya, A. Chilkoti, Angew. Chem. Int. Ed. 2015, 54, 441-445.
[18] L. Schmohl, D. Schwarzer, Curr. Opin. Chem. Biol. 2014, 22, 122-128.
[19] H. Jo, N. Meinhardt, Y. Wu, S. Kulkarni, X. Hu, K. E. Low, P. L. Davies, W. F. Degrado, D. C. Greenbaum, J. Am. Chem. Soc. 2012, 134, 17704-17713.
[20] A. Muppidi, K. Doi, S. Edwardraja, E. J. Drake, A. M. Gulick, H. G. Wang, Q. Lin, J. Am. Chem. Soc. 2012, 134, 14734-14737.
[21] P. Diderich, D. Bertoldo, P. Dessen, M. M. Khan, I. Pizzitola, W. Held, J. Huelsken, C. Heinis, ACS Chem. Biol. 2016, 11, 1422-1427.
[22] A. M. Spokoyny, Y. Zou, J. J. Ling, H. Yu, Y. S. Lin, B. L. Pentelute, J. Am. Chem. Soc. 2013, 135, 5946-5949.
[23] M. R. Jafari, L. Deng, P. I. Kitov, S. Ng, W. L. Matochko, K. F. Tjhung, A. Zeberoff, A. Elias, J. S. Klassen, R. Derda, ACS Chem. Biol. 2014, 9, 443-450.
[24] B. C. Chenna, J. R. King, B. A. Shinkre, A. L. Glover, A. L. *Lucius*, S. E. Velu, Eur. J. Med. Chem. 2010, 45, 3752-3761.
[25] K. B. Oh, S. H. Kim, J. Lee, W. J. Cho, T. Lee, S. Kim, J. Med. Chem. 2004, 47, 2418-2421.
[26] P. Timmerman, J. Beld, W. C. Puijk, R. H. Meloen, ChemBioChem 2005, 6, 821-824.
[27] C. Heinis, T. Rutherford, S. Freund, G. Winter, Nat. Chem. Biol. 2009, 5, 502-507.
[28] S. Chen, D. Bertoldo, A. Angelini, F. Pojer, C. Heinis, Angew. Chem. Int. Ed. 2014, 53, 1602-1606.
[29] B. Dang, H. Wu, V. K. Mulligan, M. Mravic, Y. Wu, T. Lemmin, A. Ford, D.-A. Silva, D. Baker, W. F. DeGrado, Proc. Natl. Acad. Sci. 2017, 201710695.
[30] M. R. Cookson, Mol. Neurodegener. 2009, 4, 9.
[31] R. Porcari, C. Proukakis, C. A. Waudby, P. Bolognesi, P. P. Mangione, J. F. S. Paton, S. Mullin, L. D. Cabrita, A. Penco, A. Relini, et al., J. Biol. Chem. 2015, 290, 2395-2404.
[32] C. B. Rosen, R. L. Kwant, J. I. MacDonald, M. Rao, M. B. Francis, Angew. Chem. Int. Ed. 2016, 55, 8585-8589.
[33] H. H. Wang, B. Altun, K. Nwe, A. Tsourkas, Angew. Chem. Int. Ed. 2017, 56, 5349-5352.
[34] R. N. De Guzman, N. K. Goto, H. J. Dyson, P. E. Wright, J. Mol. Biol. 2006, 355, 1005-1013.

Methods 1.1 Peptide Synthesis and Characterization

Peptide synthesis was performed manually on Fmoc-Rink Amid MBHA resin (Iris Biotech GmbH) according to standard Fmoc-based solid-phase peptide synthesis (SPPS) protocols. All Fmoc-protected amino acids were coupled using 4 eq. calculated to the initial amine-loading of the resin. The coupling conditions were 4 eq. of (1-cyano-2-ethoxy-2-oxoethylidenaminooxy)¬dimethylamino-morpholino-carbenium hexafluorophosphate (COMU), 4 eq. of oxyma and 8 eq. of N,N-diisopropylethylamine (DIPEA) in dimethylformamide (DMF) for the first coupling reaction (20 min). For the second coupling (45 min) 4 eq. of benzotriazole-1-yl-oxy-tris-pyrrolidino-phosphonium hexafluorophosphate (PyBOP) and 8 eq. of DIPEA in DMF were used. Fmoc-deprotection was accomplished treating the resin with a solution of 20% piperidine in DMF for 15 min. Fluorescein isothiocyanate (FITC) was coupled using 3 eq. of its isomer and 6 eq. of DIPEA in DMF for 2 h twice. Peptides were cleaved from the resin after treatment with a TFA:H2O:TIPS (95:2.5:2.5) solution (2×2 h) and precipitated with Et2O at −20° C. After lyophilization in a Freezone 4.5-105° C. freeze drying system (Labconco), the peptides were dissolved in H2O:acetonitrile (1:1) and purified in a reversed-phase semi-preparative HPLC using a Nucleodur C18 reverse-phase column (10×125 mm, 110 Å, particle size 5 µm, Macherey-Nagel; solvent A: H2O+0.1% TFA; solvent B: acetonitrile+0.1% TFA; flow rate of 6 mL min-1). Obtained products were lyophilized.

Peptide identity and purity were confirmed by HPLC/ESI-MS analysis performed in a HPLC-MS system (Agilent Technologies) provided with a Zorbax Eclipse, XDB-C18 reverse-phase column (4.6×150 mm, particle size 5 µm, Agilent; solvent A: H2O+0.1% TFA; solvent B: acetonitrile+0.1% TFA; flow rate of 1 mL min-1). The FITC labeled peptides were quantified photometrically using a V-550 UV/VIS spectrophotometer (Jasco). For the GGGK-FITC peptide, SEQ ID NO: 4, absorbance at 494 nm was measured in a 100 mM sodium phosphate buffer (pH 8.5) and concentration calculated using the extinction coefficient ε(FITC)494=77000 M-1 cm-1. For the Dabcyl-QALPET-GEK-FITC peptide, SEQ ID NO: 5, Dabcyl absorption at 494 nm was additionally taken into account (ε(Dabcyl) 494=14000 M-1 cm-1).

1.2 Protein Expression and Purification

A modified pET28a(+) vector coding for *Staphylococcus aureus* SrtA aa 60-206 was provided by AG Musacchio (Max Planck Institute, Dortmund, Germany). Variants S1-S7 were obtained either by sequence modification using site-directed mutagenesis (Quikchange™, Stratagene), restriction and ligation or in vivo cloning each resulting in the according N-terminal His6-tagged protein (FIG. 6). These constructs were transformed into *E. coli* BL21 Gold (DE3) (Agilent Technologies). Transformants were used to inoculate a Luria Broth (LB) (50 µg mL-1 kanamycin) overnight pre-culture (incubated at 37° C.). This culture was used to inoculate a Terrific Broth (TB) culture (2 L) which was incubated at 37° C. until an OD600 of 0.7 was reached. Protein expression was induced by addition of 0.5 mM IPTG and the culture was incubated overnight at 25° C. Cells were harvested by centrifugation, resuspended in lysis buffer (50 mM Tris (pH 7.5), 150 mM NaCl, 2 mM TCEP, 10% glycerol (v/v) and disrupted in a microfluidizer. The cell lysate was cleared from cell debris by centrifugation (70000 ref, 4° C., 45 min). All subsequent purification steps were performed at 4° C. SrtA and variants S1-S7 were isolated from the supernatant via FPLC affinity chromatography (HisTrap™ Fast Flow Crude 5 mL, GE Healthcare). The column was washed with 5 CV washing buffer (50 mM Tris (pH 7.5), 150 mM NaCl, 2 mM TCEP, 5% glycerol (v/v), 20 mM imidazole). Thrombin cleavage (5 U mg-1) was performed on column over night at 4° C. in Thrombin buffer (50 mM Tris (pH 8), 100 mM NaCl, 2.5 mM CaCl2), 1 mM DTT) resulting in target protein elution. To separate SrtA and variants from Thrombin enzyme size exclusion chromatography was performed (Aekta Pure, Column HiLoad 16/600 Superdex 75 pg, GE Healthcare in 20 mM HEPES (pH 7.5), 150 mM NaCl, 5 mM CaCl2, 2 mM TCEP). The purified proteins were concentrated via ultra-filtration (Amicon, Merck, 10 kDa cut off) up to 25 mg mL-1, snap frozen and stored at −80° C.

The coding sequence for an α-Synuclein (α-Syn) construct containing a C-terminal flexible linker, a SrtA recognition site as well as a His6-tag for affinity purification (FIG. 9, SEQ ID NOs: 2 and 16), was purchased as gene synthesis (Integrated DNA Technologies) and sub-cloned into a pET28a(+) vector via restriction (NcoI and XhoI) and ligation. For protein expression the vector was transformed into *E. coli* BL21 Gold (DE3). Transformants were used to inoculate an overnight LB pre-culture (50 µg mL-1 kanamycin, 37° C.). This culture was used to inoculate a kanamycin (50 µg mL-1) containing LB culture (2 L) which was incubated at 37° C. until an OD600 of 0.7 was reached. Protein expression was induced by addition of 0.5 mM IPTG and performed for 4 h at 37° C. Cells were harvested by centrifugation, resuspended in lysis buffer (50 mM Tris (pH 7.5), 150 mM NaCl) and disrupted by ultrasonication (4×30 s cycles with 1 s on 2 s off, 40% power, 0° C.). The cell lysate was cleared from cell debris by centrifugation (70000 ref, 1 h). All follow up purification steps were performed at 4° C. α-Syn was isolated from the supernatant via affinity chromatography (Aekta Pure, HisTrap™ Fast Flow Crude 5 mL, GE Healthcare). Washing was performed with lysis buffer containing 5 mM imidazole. α Syn was eluted off the column in an imidazole gradient (5 mM-500 mM). Protein containing fractions were pooled and dialyzed (Slide A Lyzer Dialysis Cassette, Thermo, 3.5 kDa cut off) overnight at 4° C. against PBS buffer (pH 7.4). Resulting pure α-Syn was concentrated via ultra filtration (Amicon, Merck, 3 kDa cut off) up to 5 mg mL-1 and subjected to fibril formation.

The coding sequences for KIX and K1 constructs (FIG. 13) containing Gateway attB1 and attB2 (Thermo) attachment and a PreScission protease recognition site, were synthesized and purchased from Integrated DNA Technologies. Afterwards, coding regions were introduced into a pDONR201 vector (BP Clonase enzyme mix, Thermo). Subsequently, LR Clonase enzyme mix (Thermo) was utilized to introduce the coding region into a pGEX-4t-3 Gateway compatible destination vector. The resulting expression vector was transformed into *E. coli* BL21 Gold (DE3). Transformants were used to inoculate an overnight LB pre-culture (100 µg mL-1 ampicillin, 37° C.) and subsequently this culture was used to inoculated an ampicillin (100 µg mL-1) containing TB culture (2 L) which was incubated at 37° C. until an OD600 of 1 was reached. Protein expression was induced by addition of 0.5 mM IPTG and performed overnight at 20° C. Cells were harvested by centrifugation, resuspended in lysis buffer (50 mM Tris (pH 7.4), 500 mM NaCl, 2 mM PMSF and 2 mM DTT) and disrupted using the microfluidizer. The cell lysate was cleared from cell debris by centrifugation (70000 ref, 4° C., 60 min). All subsequent purification steps were performed at 4° C. KIX and K1 were isolated from the supernatant via affinity chromatography (Aekta Pure, GSTPrep™ FF 16/10, GE Healthcare). Washing was performed with wash buffer (50 mM Tris (pH 7.4), 100 mM NaCl, 2 mM DTT) until baseline (OD280) was reached. PreScission cleavage was performed on column over night at 4° C. in wash buffer. Resulting target protein was concentrated via ultra-filtration up to about 6 mg mL-1 (Amicon, Merck, 3 kDa cut off, r.t.). Subsequent size exclusion chromatography was performed (Aekta Pure, Column HiLoad 16/600 Superdex 75 µg, GE Healthcare in 25 mM HEPES (pH 7.4), 100 mM NaCl, 2 mM TCEP). The purified proteins were concentrated (Amicon, Merck, 3 kDa cut off, r.t.) up to 6 mg mL-1, snap frozen and stored at −80° C.

All generated vector constructs were sequence proven by Sanger sequencing. All proteins where checked for their quality via SDS-PAGE.

1.3 α-Syn Fibril Formation and Re-Solubilization

For fibril formation, 4 mL of purified, soluble α-Syn (5 mg mL-1) were stirred at 37° C., 1250 rpm for 4 days. The resulting suspension was ultracentrifuged (135000 ref, 4° C., 45 min.) in 600 μL aliquots. The protein content of the supernatant was quantified via Nanodrop (OD280) to monitor the efficiency of fibril formation. After removal of the supernatant, the pellet was washed extensively with SrtA buffer (4 times 500 μL, 20 mM HEPES (pH 7.5), 150 mM NaCl, 5 mM CaCl2), 2 mM TCEP). For re-solubilization the fibril sample was treated either with (1 M) or without GdnHCl in SrtA buffer for 3 h at RT and gentle shaking. Supernatant was used for subsequent labeling.

1.4 α-Syn Labeling Reaction

Figure 10A:
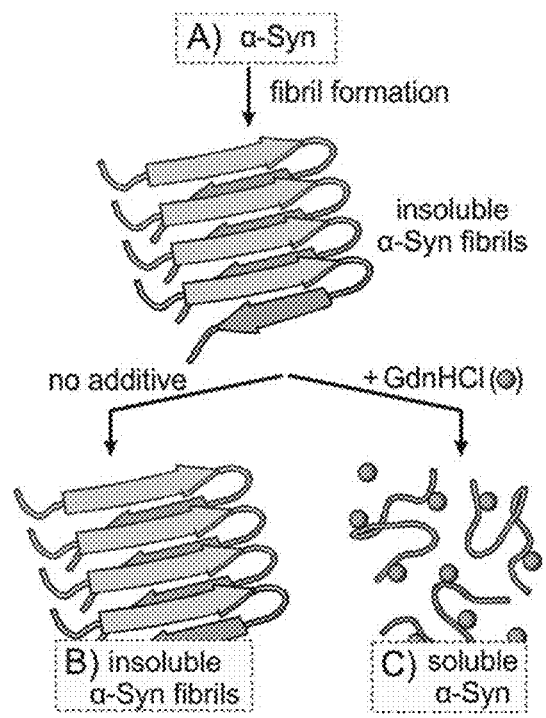
FIG. 10: a) Scheme of fibril formation and re-solubilization with GdnHCl (A: purified α-Syn prior to fibril formation, B: re-solubilization attempt in absence of GdnHCl—insoluble α-Syn fibrils, C: re-solubilized α-synuclein following GdnHCl (1 M) treatment); b) Coomassie-stained (I) and fluorescent readout (II) of full SDS-PAGE gel (17% SDS) shown in FIGS. 4d and 4e.
Figure 10B:
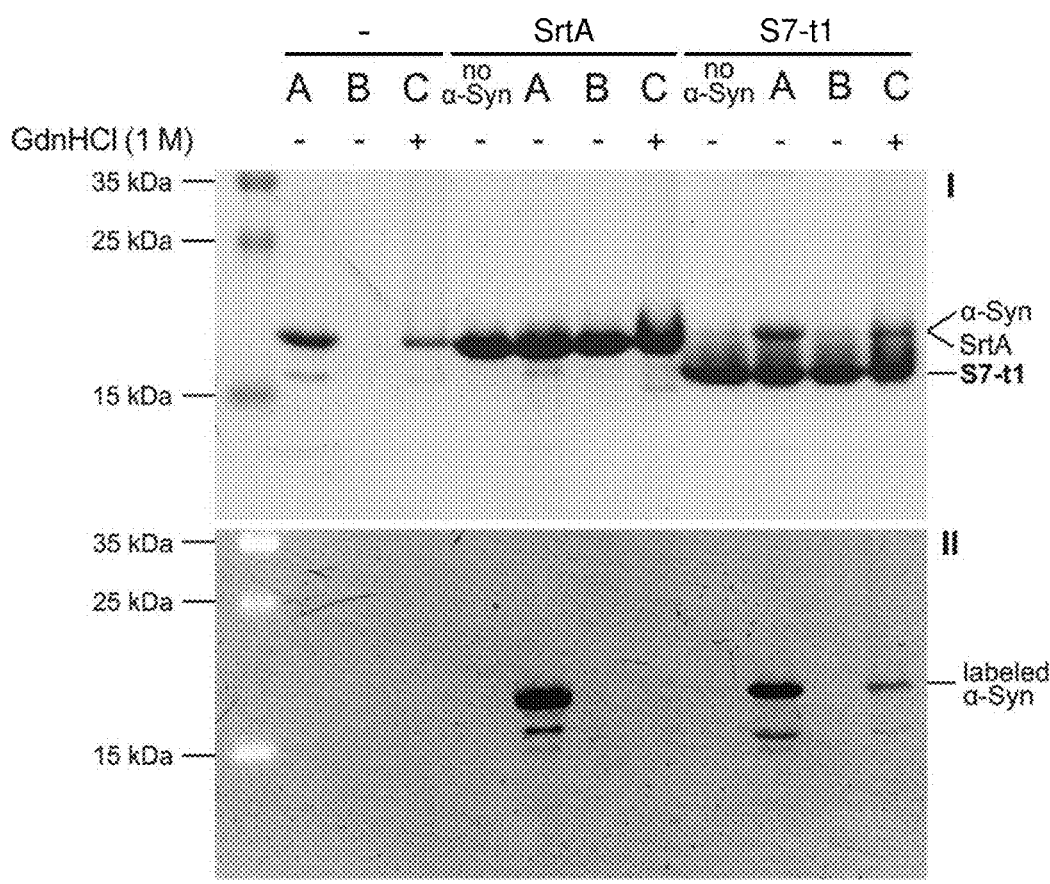

Re-solubilized α-Syn fractions were diluted 1:6 with SrtA buffer (+/−1 M GdnHCl) keeping the initial GndHCl concentration and supplemented with 2 mM GGGK-FITC and either 100 μM SrtA or S7-t1. The labeling samples were incubated for 16 h at 350 rpm and 37° C. Samples were analyzed on a SDS-PAGE gel for fluorescence in a Gel Doc XR system (BioRad). Then the gel was coomassie stained (FIG. 10).

1.5 Synthesis and Characterization of Bis- and Triselectrophilic Cross-Linkers

To a solution of K2CO3 (33 mmol, 3.3 eq.) in H2O/DCM (2:3, 18 mL) at 0° C., the corresponding diamine (10 mmol, 1 eq.) was added. The resulting mixture was allowed to cool down before the chloroacetyl chloride (22 mmol, 2.2 eq.) was added dropwise over a 1 h period at 0° C. After completed addition, the ice bath was removed and the mixture was allowed to stir at room temperature overnight. The desired product was extracted three times with DCM. Subsequently, the organic layer was washed with brine, dried over Na2SO4, filtrated and concentrated under reduced pressure. Product identity, was confirmed by NMR. For the triselectrophilic cross-linker t1 the same protocol was used with adjusted equivalents. In any crosslinking reaction, freshly prepared cross-linkers must be used.

N,N'-bis(chloroacetyl)-1,2-ethylenediamine (b1). 1H NMR (400 MHz, DMSO-d6) δ 8.27 (bs, CONH, 2H), 4.04 (s, CH2, 4H), 3.17 (m, CH2, 4H).

N,N'-bis(chloroacetyl)-1,3-propylenediamine (b2). 1H NMR (400 MHz, DMSO-d6) δ 8.20 (m, CONH, 2H), 4.04 (s, CH2, 4H), 3.10 (td, J=6.9, 5.7 Hz, CH2, 4H), 1.57 (p, J=6.9 Hz, CH2, 2H).

N,N'-bis(chloroacetyl)-1,4-butanediamine (b3). 1H NMR (400 MHz, DMSO-d6) δ 8.19 (m, CONH, 2H), 4.02 (s, CH2, 4H), 3.08 (m, CH2, 4H), 1.41 (m, CH2, 4H).

N,N'-(oxybis(ethane-2,1-diyl))bis(2-chloroacetamide) (b4). 1H NMR (400 MHz, CDCl3) δ 6.92 (bs, CONH, 2H), 4.07 (s, CH2, 4H), 3.59 (m, CH2, 4H), 3.53 (m, CH2, 4H).

N,N'-((ethane-1,2-diylbis(oxy))bis(ethane-2,1-diyl))bis(2-chloroacetamide) (b5). 1H NMR (400 MHz, DMSO-d6) δ 8.23 (m, CONH, 2H), 4.06 (s, CH2, 4H), 3.52 (m, CH2, 4H), 3.44 (t, J=5.8 Hz, CH2, 4H), 3.25 (q, J=5.8 Hz, CH2, 4H).

N,N'-(((oxybis(ethane-2,1-diyl))bis(oxy))bis(ethane-2,1-diyl))bis(2-chloroacetamide) (b6). 1H NMR (400 MHz, DMSO-d6) δ 8.23 (m, CONH, 2H), 4.06 (s, CH2, 4H), 3.52 (m, CH2, 8H), 3.44 (t, J=5.8 Hz, CH2, 4H), 3.25 (q, J=5.8 Hz, CH2, 4H).

N,N',N''-(nitrilotris(propane-3,1-diyl))tris(2-chloroacetamide) (t1). 1H NMR (400 MHz, DMSO-d6) δ 8.23 (t, J=5.6 Hz, CONH, 3H), 4.03 (s, CH2, 6H), 3.10 (q, J=6.6 Hz, CH2, 6H), 2.34 (t, J=6.9 Hz, CH2, 6H), 1.52 (p, J=7.1 Hz, CH2, 6H).

1.6 Protein Modification with Electrophiles

The reactivity of four different electrophiles with wildtype SrtA was evaluated. Thus, 50 μM SrtA was incubated with 2 mM electrophile (acrylamide 1,2-bromoacetamide 2,2-chloroacetamide 3 or 4 maleimidobutyric acid 4) in cross-linking buffer (50 mM HEPES (pH 8.5), 150 mM NaCl, 5 mM CaCl2) and 2 mM TCEP) at 35° C. and 350 rpm for 24 h. The reactions were analyzed by MS.

Protein variants S1-S6 were diluted to 50 μM in reaction buffer (50 mM HEPES (pH 8.5), 150 mM NaCl, 5 mM CaCl2) and 2 mM TCEP) and incubated with 0.5 mM biselectrophilic cross-linkers (b1-b6, 50 mM in DMSO) at 35° C. and 350 rpm for 24 h. To stop the reaction, solutions were concentrated by ultra filtration (Amicon Ultra centrifugal filters, 0.5 mL, Merck, 10 kDa cut off) and washed 5 times with SrtA buffer (20 mM HEPES (pH 7.5), 150 mM NaCl, 5 mM CaCl2), 2 mM TCEP) in order to remove the low molecular weight biselectrophilic cross-linkers, to exchange buffer and to concentrate final crosslinked protein variants. The resulting proteins were snap frozen and stored at −80° C. For the crosslinking of variant S7 with the triselectrophilic cross-linker t1, the protocol described above was applied only changing the concentration of t1 to 1 mM instead of 0.5 mM (FIG. 3b).

1.7 Measurement of Melting Temperature (Tm)

Each protein was diluted to 75 μM in 20 mM HEPES (pH 7.5), 150 mM NaCl, 5 mM CaCl2), 2 mM TCEP. Temperature was scanned (20-95° C.) in a Prometheus NT.48 (NanoTemper Technologies) at a heating rate of 1° C. min-1 using an excitation power of 35%. The ratio of fluorescence intensities at 350 nm and 330 nm (F350/F330) was plotted against the temperature and Tm-values were determined using the Nanotemper technologies protocols.

1.8 Enzymatic Hydrolysis Assay

Hydrolysis of probe Dabcyl-QALPETGEK-FITC (FIG. 7) by StrA and variants provide the cleavage product GEK-FITC which exhibits increased fluorescence. Changes in fluorescence were monitored using a Real Time PCR system (StepOnePlus™ Real-Time PCR System, Applied Biosystems) by measuring fluorescence (FAM channel, 520 nm) at the given temperature (in 10 min steps over 16 h). Enzymes were diluted to 20 μM in SrtA buffer (20 mM HEPES (pH 7.5), 150 mM NaCl, 5 mM CaCl2), 2 mM TCEP) supplemented with TWEEN (final concentration 0.01%). Resulting enzyme solutions were mixed 1:1 with a 20 μM solution of the peptidic probe (Dabcyl-QALPETGEK-FITC) in the same buffer (final volume 20 μL, 10 μM probe, 10 μM enzyme). A sample without enzyme was used as blank. Fluorescence readout was background substracted and plotted against time. The slope of the linear part of the curve was determined (v) as a measure of enzymatic activity. Subsequently, v-values were divided by v(SrtA) to obtain relative activities.

1.9 Enzymatic Transpeptidation Assay

Fluorescent Readout

This assay was performed analogously to the hydrolysis assay described above, but in presence of 2.5 mM triglycine (G3, Sigma-Aldrich). To perform the thermal activity profile of SrtA and S7-t1, transpeptidation activity was determined at various temperatures (37° C., 45° C., 55° C., 60° C., 65° C., 70° C., 75° C.). Triplicates were measured, averaged and plotted with error bars (1 σ). Statistical significance was evaluated by an unpaired t-test (GraphPad). We considered p-values <0.05 as statistically significant (ns: not significant, *p<0.05, p<0.01, *p<0.001, FIG. 4b).

HPLC-MS Monitoring of Transpeptidation Activity

Reactions were performed at 65° C. for SrtA and S7-t1. Reaction conditions: 50 μM POI (SrtA or S7-t1); 10 μM peptidic probe (Dabcyl-QALPETGEK-FITC); 2.5 mM G3 in SrtA buffer (20 mM HEPES (pH 7.5), 150 mM NaCl, 5 mM CaCl2), 2 mM TCEP); 65° C., 12 h, 350 rpm. The reaction mixture was quenched by addition of 1% TFA. The products of these reactions were analyzed by HPLC-MS (FIG. 4a).

Transpeptidation Activity in the Presence of GdnHCl

Transpeptidation activity efficiency in the presence of the denaturing agent GdnHCl was evaluated for SrtA and S7-t1. Transpeptidation activity at fixed POI (10 μM), peptidic probe (10 μM) and G3 (2.5 mM) concentrations and at fix temperature (37° C.) was measured at several GdnHCl concentrations (0 M, 0.5 M, 0.75 M, 1.0 M, 1.5 M and 2.0 M). Triplicates were measured, averaged and plotted with error bars (1 σ). Statistical significance was evaluated by an unpaired t-test (GraphPad). We considered p-values <0.05 as statistically significant (ns: not significant, *p<0.05, p<0.01, *p<0.001, FIG. 4c).

1.10 Folding Reversibility of SrtA and S7-t1

SrtA and S7-t1 were diluted to 20 μM in 20 mM HEPES, pH 7.5, 150 mM NaCl, 5 mM CaCl2), 2 mM TCEP and 0.01% TWEEN 20. These solutions were heated from r.t. to 85° C. over 30 min in a ThermoMixer (HTA-BioTec), and then cooled down to r.t. over 60 min. Afterwards, the proteins were evaluated for transpeptidation activity at 37° C. together with freshly prepared solutions of non-preheated proteins.

1.11 HPLC-Coupled High-Resolution Mass Spectrometry

Unmodified S7 and bicyclic S7-t1 were incubated first with 1 mM DTT then with 5.5 mM iodoacetamide, denatured in 8 M Urea and finally digested. First, LysC (Wako™, Osaka, Japan) was used for 3 hours (protein-to-enzyme ratio 50:1) and after dilution with 4 volumes of 50 mM ammonium bicarbonate (AMBIC, pH 8.3) to a final concentration of 2.0 M urea, peptides were digested overnight at 37° C. with sequencing-grade modified trypsin (Promega™, Madison, Wis.; protein-to-enzyme ratio 50:1). Peptides were desalted on C18 stage tips and 100-300 ng of peptide were separated with a PepMap100 RSLC C18 nano-HPLC column (2 m, 100 Å, 75 ID×25 cm, nanoViper, Dionex, Germany) on an UltiMate™ 3000 RSLCnano system (ThermoFisher Scientific, Germany) using a 65 min gradient from 5-60% acetonitrile with 0.1% formic acid and then directly sprayed via a nano-electrospray source (Nanospray Flex Ion Scource, Thermo Scientific) in a Q Exactive™ Hybrid Quadrupole-Orbitrap Mass Spectrometer HF (ThermoFisher Scientific). For coupling of the nano-HPLC to the Quadrupole-Orbitrap Mass Spectrometer, a standard coated Silica-Tip (ID 20 m, Tip-ID 10 m, New Objective, Woburn, Mass., USA) was used. The Q Exactive™ HF was operated in a data-dependent mode acquiring one survey scan and subsequently ten MS/MS scans. MS spectra were acquired with a mass range from 300 to 1650 m/z with a resolution of 70000, followed by up to then high energy collision dissociation (HCD) MS/MS scans at a resolution of 17500. Resulting raw files were processed with the MaxQuant software (version 1.5.2.18) including the *Andromeda* search algorithm searching against S7 using deamidation (de, for Asn and Gln), oxidation (ox, for Met), carbamidomethylation (ca, for Cys) and t1 remnant (cl, C2H2O[—H] for Cys) as variable modifications. The mass accuracy for full mass spectra was set to 20 ppm for the first and to 4.5 ppm for the second search and to 20 ppm for MS/MS spectra. Two miscleavages were allowed. A false discovery rate cut off of 1% was applied at the peptide and site decoy fraction.

1.12 Fluorescence Polarization Assay (FP)

Binding of K1-t1 and K1-t2 to mixed lineage leukemia (MLL) transcription factor was evaluated using the FITC-labeled peptide FITC-020c-GNILPSDI(Nle)DFVLKNTP-NH2 (SEQ ID NO: 6). This sequence is derived from MLL and will be refereed as MLL peptide throughout. A 40 nM solution of MLL peptide in 25 mM HEPES (pH 7.4), 100 mM NaCl and 2 mM TCEP was prepared. A 3-fold dilution of KIX, K1-t1 and K1-t2 was performed in 14 steps on a 384-well-plate (black, round bottom, Corning) using the same buffer. 5 μL of 40 nM MLL peptide solution was then added, and the final 20 μL solution was incubated at r.t. A final protein range of 70 μM-0 μM was used. After 1 h-incubation, fluorescence polarization was measured using a Spark 20M plate reader (Tecan) with λ(ex)=485 nm and λ(em)=525 nm. Kd were determined by applying nonlinear regression analysis of dose-response curves in GraphPad Prism software.

Example 2

Aldehyde dehydrogenases (ALDHs) have been applied for their highly chemoselective oxidation of aldehyde moieties to carboxylic acids on many different substrate molecules [T. Knaus, V. Tseliou, L. D. Humphreys, N. S. Scrutton, F. G. Mutti, Green Chemistry 20181]. The melting temperature is slightly above 47° C., meaning that only after two to four hours, the catalytic activity of ALDH is significantly reduced. Cross-linked ALDH can help to improve thermal stability of the enzyme and increase its "longevity" during biocatalytic oxidation. ALDH from bovine lens (ALDH-Bov) forms a homodimer and/or -tetramer, of which the quarternary structure is available. To crosslink three monomers of the multimer, an ALDH-Bov polypeptide is designed having cysteines at positions 73, 414, 499, to crosslink two monomers of the multimer, an ALDH-Bov polypeptide is designed having cysteines at positions 72, 238, 448 with reference to amino acid position numbering of ALDH-Bov polypeptide having the amino acid sequence:

```
                                              (SEQ ID NO: 7)
MSSSAMPDVPAPLTNLQFKYTKIFINNEWHSSVSGKKFPVFNPATEEKLC

EVEEGDKEDVDKAVKAARQAFQIGSPWRTMDASERGRLLNKLADLIERDH

LLLATMEAMNGGKLFSNAYLMDLGGCIKTLRYCAGWADKIQGRTIPMDGN

FFTYTRSEPVGVCGQIIPWNFPLLMFLWKIGPALSCGNTVVVKPAEQTPL

TALHMGSLIKEAGFPPGVVNIVPGYGPTAGAAISSHMDVDKVAFTGSTEV

GKLIKEAAGKSNLKRVSLELGGKSPCIVFADADLDNAVEFAHQGVFYHQG

QCCIAASRLFVEESIYDEFVRRSVERAKKYVLGNPLTPGVSQGPQIDKEQ

YEKILDLIESGKKEGAKLECGGGPWGNKGYFIQPTVFSDVTDDMRIAKEE

IFGPVQQIMKFKSLDDVIKRANNTFYGLSAGIFTNDIDKAITVSSALQSG

TVWVNCYSVVSAQCPFGGFKMSGNGRELGEYGFHEYTEVKTVTIKISQKN

S.
```

Such crosslinked ALDH-Bov polypeptides are expected to have increased thermal stability.

The invention claimed is:

1. A method for increasing the stability of a native or modified polypeptide or combination of polypeptides against denaturation, wherein the polypeptide or combination of polypeptides exhibits a natural tertiary structure having at least two secondary structures, said method comprising:
   a) identifying within the polypeptide or combination of polypeptides in its natural tertiary structure three cysteine residues being located in the at least two distinct secondary structures having a spacial proximity for reaction with a trivalent thiol-reactive cross-linker having a C3 symmetric core, and
   b) contacting said polypeptide or combination of polypeptides with the trivalent thiol-reactive cross-linker such that the linker forms covalent bonds with each of the three cysteine residues in a manner to stabilize the natural tertiary structure of the polypeptide or combination of polypeptides against denaturation compared to the stability of the polypeptide or combination of polypeptides without the reacted cross-linker, wherein the alpha-C atoms of the three cysteine residues form a triangle with side lengths between 6 to 23 Angstroms.

2. The method of claim 1, wherein in step a) one or more of the three cysteine residues are introduced to the polypeptide or combination of polypeptides to create a modified polypeptide or combination of polypeptides.

3. The method of claim 1, wherein said polypeptide or combination of polypeptides comprises at least a fourth cysteine residue and wherein said method does not result in the formation of a covalent bond between the fourth cysteine and the cross-linker.

4. The method of claim 1, wherein the cross-linker has formula (I):

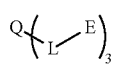 (I)

wherein

Q is a core structure of

each dashed line in Q indicating a site where Q is bound to L, each L is

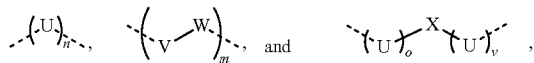

wherein each U is independently selected from $CH_2$ and $CF_2$, n is an integer in the range of 2-8, each dashed line in L indicating a site where L is bound to Q or E, each E is

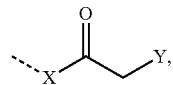

wherein each X is NH,

Y is each dashed line in E indicating a site where E is bound to L.

5. The method of claim 1, wherein the cross-linker has formula (III):

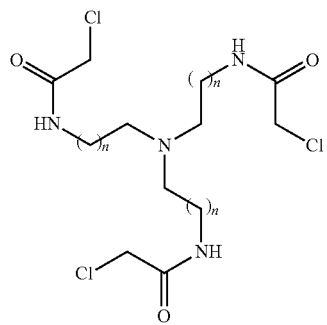

wherein n is 1 or n is 2.

* * * * *